(12) United States Patent
Rennert

(10) Patent No.: US 7,597,887 B2
(45) Date of Patent: Oct. 6, 2009

(54) KIM-1 ANTAGONISTS AND USE TO MODULATE IMMUNE SYSTEM

(75) Inventor: Paul D. Rennert, Holliston, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 139 days.

(21) Appl. No.: 10/540,959

(22) PCT Filed: Dec. 29, 2003

(86) PCT No.: PCT/US03/41294

§ 371 (c)(1),
(2), (4) Date: Apr. 4, 2006

(87) PCT Pub. No.: WO2004/060041

PCT Pub. Date: Jul. 22, 2004

(65) Prior Publication Data

US 2006/0222648 A1 Oct. 5, 2006

Related U.S. Application Data

(60) Provisional application No. 60/436,934, filed on Dec. 30, 2002.

(51) Int. Cl.
*A61K 39/395* (2006.01)
(52) U.S. Cl. ............... 424/130.1; 424/133.1; 424/144.1
(58) Field of Classification Search .................. None
See application file for complete search history.

(56) References Cited

U.S. PATENT DOCUMENTS

| | | | |
|---|---|---|---|
| 5,622,861 A | 4/1997 | Kaplan et al. | |
| 6,084,083 A | 7/2000 | Levinson | |
| 6,664,385 B1 | 12/2003 | Sanicola-Nadel et al. | |
| 2003/0124114 A1 | 7/2003 | McIntire et al. | |
| 2003/0215831 A1 | 11/2003 | Sanicola-Nadel et al. | |
| 2004/0005322 A1 | 1/2004 | Kuchroo et al. | |
| 2004/0180038 A1 | 9/2004 | Hancock et al. | |
| 2005/0014687 A1* | 1/2005 | Anderson et al. ............. 514/12 |
| 2005/0095593 A1 | 5/2005 | McIntire et al. | |
| 2005/0112117 A1 | 5/2005 | Bailly et al. | |
| 2005/0276756 A1* | 12/2005 | Hoo et al. .................. 424/1.49 |

FOREIGN PATENT DOCUMENTS

| | | |
|---|---|---|
| EP | 1062949 | 12/2000 |
| WO | WO 96/04376 | 2/1996 |
| WO | WO 97/44459 | 11/1997 |
| WO | WO 97/44460 | 11/1997 |
| WO | WO 98/20110 | 5/1998 |
| WO | WO 01/98481 | 12/2001 |
| WO | WO 02/098920 | 12/2002 |
| WO | WO 03/025138 | 3/2003 |
| WO | WO 03/042661 | 5/2003 |
| WO | WO 03/080856 | 10/2003 |
| WO | WO 2004/005544 | 1/2004 |
| WO | WO 2004/084823 | 10/2004 |
| WO | WO 2005/001092 | 1/2005 |

OTHER PUBLICATIONS

Xiao et al. Differential engagement of Tim-1 during activation can positively or negatively costimulate T cell expansion and effector function. J Exp Med. Jul. 9, 2007;204(7):1691-702.*
Umetsu et al. TIM-1 induces T cell activation and inhibits the development of peripheral tolerance. Nat Immunol. May 2005;6(5):447-54.*
Hoo et al. Vaccination with cell immunoglobulin mucin-1 antibodies and inactivated influenza enhances vaccine-specific lymphocyte proliferation, interferon-gamma production and cross-strain reactivity. Clin Exp Immunol. Jul. 2006;145(1):123-9.*
Stites et al. Basic and Clinical Immunlogy, 8th edition, pp. 30-31,208-209, 246-247, 1994.*
Piccotti Jr et al. Interleukin-12 (IL-12)-driven alloimmune. Transplantation. Jun. 15, 1999;67(11):1453-60.*
Campo Ca et al. Zinc inhibits the mixed lymphocyte culture. Biol Trace Elem Res. Jan. 2001;79(1):15-22.*
Reinsmoen et al. Evaluation of the Cellular Immune Response in Transplantation. In Manual of Clinical Laboratory Immunology, 6th Edition, by Rose, N. R., pp. 1164-1175, 1994.*
Bailly, V., et al., "Shedding of Kidney Injury Molecule-1, a Putative Adhesion Protein Involved in Renal Regeneration," Journal of Biological Chemistry, (2002) 277(42):39739-39748.
Berg et al., "L-selectin-mediated Lymphocyte Rolling on MadCAM-1," Nature (1993) 366:695-698.
Berlin et al., "alpha-4-beta-7 Integrin Mediates Lymphocyte Binding to the Mucosal Vascular Address in MAdCAM-1," Cell (1993) 74:185-195.
Bonventre and Colvin, "Adhesion Molecules in Renal Disease," Current Opinion in Nephrology and Hypertension (1996) 5:254-261.
Briskin et al., "MAdCAM-1 has Homology to Immunoglobulin and Mucin-like Adhesion Receptors and to IgA1," Nature (1993) 363:461-464.
Database No. AC005603, *Homo sapiens* subtelomeric cosmid 11b-1,Sep. 3, 1998.

(Continued)

*Primary Examiner*—Maher M Haddad
(74) *Attorney, Agent, or Firm*—Fish & Richardson P.C.

(57) ABSTRACT

The use of KIM-1 antagonists to inhibit signaling between a T cell and a second cell, e.g., an antigen-presenting cell, is disclosed. Such inhibition is useful for treatment of diseases including various autoimmune diseases and graft-versus-host disease. Also disclosed is the use of a KIM-1 antagonist to inhibit secretion of IFN-γ by lymphocytes or other immune cells in a mammal. Inhibition of IFN-γ is useful for treatment of inflammatory diseases or disorders, e.g., inflammatory bowel disease.

4 Claims, 14 Drawing Sheets

OTHER PUBLICATIONS

Database Accession No. AC026777, *Homo sapiens* chromosome 5 clone CTC-332D4, complete sequence, retrieved from EMBL, Mar. 27, 2000.

Database Accession No. AQ277590, "CITBI-E1-2517G14. TFCITBI-E1 *Homo sapiens* genomic clone 2517G14, genomic survey sequence," retrieved from EMBL, Nov. 23, 1998.

Database Accession No. AL022721, "Human DNA Sequence from clone 109F14 on chromosome 6p21.2-21.3", retrieved from EMBL, Apr. 27, 1998.

Dudley et al., "A Requirement for Bone Morphogenetic Protein-7 During Development of the Mammalian Kidney and Eye," Genes & Development (1995) 9:2795-2807.

Encinas et al., "Anti-T-Cell Ig and mucin domain-containing protein 1 antibody decreases $T_H2$ airway inflammation in a mouse model of asthma.", J. of Allergy and Clinical Immunol. (2005), 116(6):1343-1349, (XP002367404).

Faure et al., "Differentially Expressed Genes in Ischemic Acute Renal Failure", Mol. Biol. Of the Cell, Bethesda, MD, 1998, 9:473A (XP-000953127).

Fagotto and Gumbiner, "Cell Contact-Dependent Signaling," Developmental Biology (1996) 180:445-454.

Feigelstock et al., "The human homolog of HAVcr-1 codes for a hepatitis A virus cellular receptor," J. Virol. (1998) 72:6621-6628.

Ferrara et al., "Monoclonal Antibody And Receptor Antagonist Therapy for GVHD.", Cancer Treatment and Research, (1999), 101:331-368.

Greve et al., "The Major Human Rhinovirus Receptor Is ICAM-1," Cell (1989) 56:839-847.

Gorczynski et al., "A CD200FC Immunoadhesin Prolongs Rat Islet Xenograft Survival in Mice.", Transplantation, Williams and Wilkins, Baltimore, MD, US., (2002), 73(12):1948-1953.

Han, W. et al., "Kidney Injury Molecule-1 (KIM-1): A novel biomarker for human renal proximal tubule injury," Kidney International, (2001, 62(1):237-244.

Hubank and Schatz. "Identifying Differences in mRNA Expression by Representational Difference Analysis of cDNA," Nucleic Acids Research (1994) 22:5640-5648.

Ichimura et al., "Kidney Injury Molecule-1 (KIM-1), a Putative Epithelial Cell Adhesion Molecule . . .". J. Biol. Chem. 273(7):4135-4142, 1998.

Kaplan et al. "Identification of a Surface Glycoprotein on African Green Monkey Kidney Cells as a Receptor for Hepatitis A Virus," EMBO (1996) 15:4282-96.

Klinken et al, "Mucin Gene Structure and Expression: Protection vs. Adhesion," Am J. Physiol. (1995) 269:G613-G627.

Kuchroo, et al. "The *Tim* Gene Family: Emerging Roles in Immunity and Disease," Nat. Rev. Immunol. (2003) 3:454-62.

Kumanogoh et al. "Class IV semaphorin Sema4A enhances T-cell activation and interacts with Tim-2" Nature (2002) 419:629-33.

Lin G. et al., "Expression of CD34 in endothelial cells, hematopoietic progenitors and nervous cells in fetal and adult mouse tissues" Eur. J. Immunol. (1995) 25:1508-1516.

Luo et al., "BMP-7 is an Inducer of Nephrogenesis and is also Required for Eye Development and Skeletal Patterning," Genes & Development (1995) 9:2808-2820.

McIntire et al. "Identification of *Tapr* (An Airway Hyperreactivity Regulator Locus) and the Linked *Tim* Gene Family," Nat. Immunol. (2001):2:1109-16.

Monney et al., "Th1-Specific Cell Surface Protein Tim-3 Regulates Macrophage Activation and Severity of an Autoimmune Disease," Nature (2002) 415:536-41.

Muller et al., "Integrin alpha8-beta1 is Critically Important for Epithelial-Mesenchymal Interactions During Kidney Morphogenesis" Cell (1997) 88:603-613.

Owens et al., "The genetic engineering of monoclonal antibodies," J. Immunol. Methods. (1994) 168:149-165.

Padanilam et al., Molecular mechanisms of cell death and regeneration in acute ischemic renal injury, Current Opinion in Nephrology and Hypertension, Rapid Science, London GB 1999, 81(1):15-19 (XP-000953223).

Prinz et al., "Treatment of severe cutaneous lupus erythematosus with a chimeric CD4 monoclonal antibody, cM-T412.", J. of the American Academy of Dermatology, (1996), 34:244-52.

Rieger et al., Glossary of Genetics. 5th Edition, Springer-Verlag, NY, (1991) 16-17.

Rosenberg et al., "Differential gene expression in the recovery from the ischemic renal injury", Kidney International 39:1156-1161, 1991 (XP-000953186).

Rudikoff et al., "Single amino acid substitution altering antigen-binding specificity." Proc. Nat. Acad. Sci., USA, (1982) 79:1979-1983.

Sastry and Horwitz, "Adhesion-Growth Factor Interactions During Differentiation: An Integrated Biological Response," Developmental Biology (1996) 180:455-467.

Shimizu et al., "Mucins in the Mainstream," Nature (1993) 336:630-631.

Shyjan et al., "Human Mucosal Addressin Cell Adhesion Molecule-1 (MAdCAM-1) Demonstrates Structural and Functional Similarities to the alpha-4-beta-7-Integrin Binding Domains of Murine MAdCAM-1," J. of Immunology (1996) 156:2851-2857.

Skolnick et al., "From genes to protein structure and function: novel applications of computational approaches in the genomic era," Tibtech (2000) 18:34-39.

Silberstein et al., "Neutralization of Hepatitis A Virus (HAV) by an Immunoadhesin Containing the Cysteine-Rich Region of HAV Cellular Receptor-1.", J. of Virol. (2001), 75(2):717-725.

Takada et al., "The Cytokine-adhesion Molecule Cascade in Ischemia/Reperfusion Injury of the Rat Kidney," J. Clin. Invest. (1997) 99:2682-2690.

Thadhani et al., "Acute Renal Failure," NEJM (1996) 334:1448-1460.

Thompson et al., The Cys-Rich Region of Hepatitis A Virus Cellular Receptor 1 is Required for Binding of Hepatitis A Virus and Protective Monoclonal Antibody 190/4, J. of Virology (1998) 72(5):3751-3761.

Weterman et al., "nmb, A Novel Gene, is Expressed in Low-Metastatic Human Melanoma Cell Lines and Xenografts," Int. J. Cancer (1995) 60:73-81.

Wills-Karp "Asthma genetics: not for the TIMid?" (2001) Nat Immunol. 2001 2(12):1095-96.

Yung, R., "Etanercept," Current Opinion in Investigational Drugs, Pharmapress, U.S., (Feb. 2001), 2(2):216-221.

Brams, P. et al., "A humanized anti-human CD154 monoclonal antibody blocks CD154-CD40 mediated human B cell activation," International Immunopharmacology Elsevier, Amsterdam, NL (2001), 1(2):277-294.

Saxena, M. et al., "Inhibition of T cell signaling by mitogen-activated protein kinase-targeted hematopoietic tyrosine phosphatase (HePTO)," The Journal of Biological Chemistry (1999), 274(17):11693-11700.

Umetsu Dale, T. et al., "Asthma: an epidemic of dysregulated immunity," Nature Immunology (2002, 3(8):715-720.

Xia T., et al., "Cimetidine inhibits production of interferon gamma and tumor necrosis factor alpha by splenocytes in aplastic anemic mice," Acta Pharmacologica Sinica (2001), 22(3):239-242.

Deng, B. et al., "An Agonist Murine Monoclonal Antibody to the Human c-Mpl Receptor Stimulates Megakaryocytopoiesis," *Blood*, 1998, 92(6):1981-1988.

Totpal, K. et al., "TNF and Its Receptor Antibody Agonist Differ in Mediation of Cellular Responses," *The Journal of Immunology*, 1994, 153(5):2248-2257.

* cited by examiner

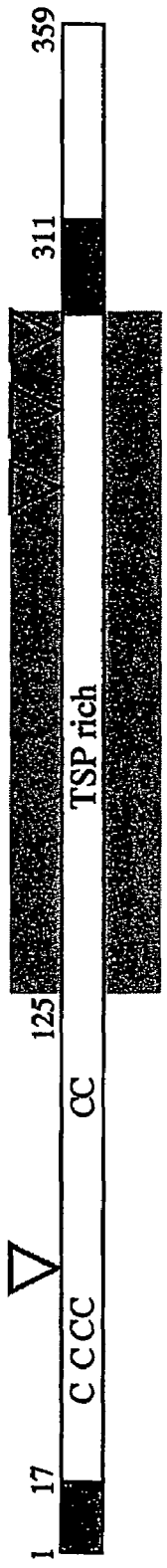

SEQUENCE LISTING

```
<160> NUMBER OF SEQ ID NOS: 9

<210> SEQ ID NO 1
<211> LENGTH: 359
<212> TYPE: PRT
<213> ORGANISM: Homo sapiens

<400> SEQUENCE: 1

Met His Pro Gln Val Val Ile Leu Ser Leu Ile Leu His Leu Ala Asp
 1               5                  10                  15

Ser Val Ala Gly Ser Val Lys Val Gly Gly Glu Ala Gly Pro Ser Val
                20                  25                  30

Thr Leu Pro Cys His Tyr Ser Gly Ala Val Thr Ser Met Cys Trp Asn
            35                  40                  45

Arg Gly Ser Cys Ser Leu Phe Thr Cys Gln Asn Gly Ile Val Trp Thr
        50                  55                  60

Asn Gly Thr His Val Thr Tyr Arg Lys Asp Thr Arg Tyr Lys Leu Leu
    65                  70                  75                  80

Gly Asp Leu Ser Arg Arg Asp Val Ser Leu Thr Ile Glu Asn Thr Ala
                85                  90                  95

Val Ser Asp Ser Gly Val Tyr Cys Cys Arg Val Glu His Arg Gly Trp
            100                 105                 110
```

```
Phe Asn Asp Met Lys Ile Thr Val Ser Leu Glu Ile Val Pro Pro Lys
            115                 120                 125

Val Thr Thr Thr Pro Ile Val Thr Thr Val Pro Thr Val Thr Thr Val
        130                 135                 140

Arg Thr Ser Thr Thr Val Pro Thr Thr Thr Thr Val Pro Thr Thr Thr
145                 150                 155                 160

Val Pro Thr Thr Met Ser Ile Pro Thr Thr Thr Val Pro Thr Thr
                165                 170                 175

Met Thr Val Ser Thr Thr Thr Ser Val Pro Thr Thr Ser Ile Pro
            180                 185                 190

Thr Thr Thr Ser Val Pro Val Thr Thr Val Ser Thr Phe Val Pro
        195                 200                 205

Pro Met Pro Leu Pro Arg Gln Asn His Glu Pro Val Ala Thr Ser Pro
    210                 215                 220

Ser Ser Pro Gln Pro Ala Glu Thr His Pro Thr Thr Leu Gln Gly Ala
225                 230                 235                 240

Ile Arg Arg Glu Pro Thr Ser Ser Pro Leu Tyr Ser Tyr Thr Thr Asp
                245                 250                 255

Gly Asn Asp Thr Val Thr Glu Ser Ser Asp Gly Leu Trp Asn Asn Asn
            260                 265                 270

Gln Thr Gln Leu Phe Leu Glu His Ser Leu Leu Thr Ala Asn Thr Thr
        275                 280                 285

Lys Gly Ile Tyr Ala Gly Val Cys Ile Ser Val Leu Val Leu Leu Ala
    290                 295                 300

Leu Leu Gly Val Ile Ile Ala Lys Lys Tyr Phe Phe Lys Lys Glu Val
305                 310                 315                 320

Gln Gln Leu Ser Val Ser Phe Ser Ser Leu Gln Ile Lys Ala Leu Gln
                325                 330                 335

Asn Ala Val Glu Lys Glu Val Gln Ala Glu Asp Asn Ile Tyr Ile Glu
            340                 345                 350

Asn Ser Leu Tyr Ala Thr Asp
    355

<210> SEQ ID NO 2
<211> LENGTH: 334
<212> TYPE: PRT
<213> ORGANISM: Homo sapiens

<400> SEQUENCE: 2

Met His Pro Gln Val Val Ile Leu Ser Leu Ile Leu His Leu Ala Asp
1               5                   10                  15

Ser Val Ala Gly Ser Val Lys Val Gly Gly Glu Ala Gly Pro Ser Val
            20                  25                  30

Thr Leu Pro Cys His Tyr Ser Gly Ala Val Thr Ser Met Cys Trp Asn
        35                  40                  45

Arg Gly Ser Cys Ser Leu Phe Thr Cys Gln Asn Gly Ile Val Trp Thr
    50                  55                  60

Asn Gly Thr His Val Thr Tyr Arg Lys Asp Thr Arg Tyr Lys Leu Leu
65                  70                  75                  80

Gly Asp Leu Ser Arg Arg Asp Val Ser Leu Thr Ile Glu Asn Thr Ala
                85                  90                  95

Val Ser Asp Ser Gly Val Tyr Cys Cys Arg Val Glu His Arg Gly Trp
            100                 105                 110

Phe Asn Asp Met Lys Ile Thr Val Ser Leu Glu Ile Val Pro Pro Lys
```

```
                115                 120                 125
Val Thr Thr Thr Pro Ile Val Thr Thr Val Pro Thr Thr Val
    130                 135                 140

Arg Thr Ser Thr Thr Val Pro Thr Thr Thr Val Pro Thr Thr
145                 150                 155                 160

Val Pro Thr Thr Met Ser Ile Pro Thr Thr Thr Val Pro Thr Thr
                165                 170                 175

Met Thr Val Ser Thr Thr Ser Val Pro Thr Thr Ser Ile Pro
            180                 185                 190

Thr Thr Thr Ser Val Pro Val Thr Thr Val Ser Thr Phe Val Pro
        195                 200                 205

Pro Met Pro Leu Pro Arg Gln Asn His Glu Pro Val Ala Thr Ser Pro
    210                 215                 220

Ser Ser Pro Gln Pro Ala Glu Thr His Pro Thr Thr Leu Gln Gly Ala
225                 230                 235                 240

Ile Arg Arg Glu Pro Thr Ser Ser Pro Leu Tyr Ser Tyr Thr Thr Asp
                245                 250                 255

Gly Asn Asp Thr Val Thr Glu Ser Ser Asp Gly Leu Trp Asn Asn Asn
            260                 265                 270

Gln Thr Gln Leu Phe Leu Glu His Ser Leu Leu Thr Ala Asn Thr Thr
        275                 280                 285

Lys Gly Ile Tyr Ala Gly Val Cys Ile Ser Val Leu Val Leu Leu Ala
    290                 295                 300

Leu Leu Gly Val Ile Ile Ala Lys Lys Tyr Phe Phe Lys Lys Glu Val
305                 310                 315                 320

Gln Gln Leu Arg Pro His Lys Ser Cys Ile His Gln Arg Glu
                325                 330

<210> SEQ ID NO 3
<211> LENGTH: 518
<212> TYPE: PRT
<213> ORGANISM: Artificial Sequence
<220> FEATURE:
<223> OTHER INFORMATION: Human KIM-1 Extracellular Domain Fc Construct

<400> SEQUENCE: 3

Met His Pro Gln Val Val Ile Leu Ser Leu Ile Leu His Leu Ala Asp
1               5                   10                  15

Ser Val Ala Gly Ser Val Lys Val Gly Gly Glu Ala Gly Pro Ser Val
            20                  25                  30

Thr Leu Pro Cys His Tyr Ser Gly Ala Val Thr Ser Met Cys Trp Asn
        35                  40                  45

Arg Gly Ser Cys Ser Leu Phe Thr Cys Gln Asn Gly Ile Val Trp Thr
    50                  55                  60

Asn Gly Thr His Val Thr Tyr Arg Lys Asp Thr Arg Tyr Lys Leu Leu
65                  70                  75                  80

Gly Asp Leu Ser Arg Arg Asp Val Ser Leu Thr Ile Glu Asn Thr Ala
                85                  90                  95

Val Ser Asp Ser Gly Val Tyr Cys Cys Arg Val Glu His Arg Gly Trp
            100                 105                 110

Phe Asn Asp Met Lys Ile Thr Val Ser Leu Glu Ile Val Pro Pro Lys
        115                 120                 125

Val Thr Thr Thr Pro Ile Val Thr Thr Val Pro Thr Val Thr Thr Val
    130                 135                 140

Arg Thr Ser Thr Thr Val Pro Thr Thr Thr Val Pro Thr Thr Thr
```

-continued

```
                145                 150                 155                 160
Val Pro Thr Thr Met Ser Ile Pro Thr Thr Thr Val Pro Thr Thr
                165                 170                 175

Met Thr Val Ser Thr Thr Thr Ser Val Pro Thr Thr Ser Ile Pro
                180                 185                 190

Thr Thr Thr Ser Val Pro Val Thr Thr Val Ser Thr Phe Val Pro
                195                 200                 205

Pro Met Pro Leu Pro Arg Gln Asn His Glu Pro Val Ala Thr Ser Pro
                210                 215                 220

Ser Ser Pro Gln Pro Ala Glu Thr His Pro Thr Thr Leu Gln Gly Ala
225                 230                 235                 240

Ile Arg Arg Glu Pro Thr Ser Ser Pro Leu Tyr Ser Tyr Thr Thr Asp
                245                 250                 255

Gly Asn Asp Thr Val Thr Glu Ser Ser Asp Gly Leu Trp Asn Asn Asn
                260                 265                 270

Gln Thr Gln Leu Phe Leu Glu His Ser Leu Leu Thr Ala Asn Thr Thr
                275                 280                 285

Lys Gly Val Asp Lys Thr His Thr Cys Pro Pro Cys Pro Ala Pro Glu
                290                 295                 300

Leu Leu Gly Gly Pro Ser Val Phe Leu Phe Pro Pro Lys Pro Lys Asp
305                 310                 315                 320

Thr Leu Met Ile Ser Arg Thr Pro Glu Val Thr Cys Val Val Val Asp
                325                 330                 335

Val Ser His Glu Asp Pro Glu Val Lys Phe Asn Trp Tyr Val Asp Gly
                340                 345                 350

Val Glu Val His Asn Ala Lys Thr Lys Pro Arg Glu Glu Gln Tyr Asn
                355                 360                 365

Ser Thr Tyr Arg Val Val Ser Val Leu Thr Val Leu His Gln Asp Trp
                370                 375                 380

Leu Asn Gly Lys Glu Tyr Lys Cys Lys Val Ser Asn Lys Ala Leu Pro
385                 390                 395                 400

Ala Pro Ile Glu Lys Thr Ile Ser Lys Ala Lys Gly Gln Pro Arg Glu
                405                 410                 415

Pro Gln Val Tyr Thr Leu Pro Pro Ser Arg Asp Glu Leu Thr Lys Asn
                420                 425                 430

Gln Val Ser Leu Thr Cys Leu Val Lys Gly Phe Tyr Pro Ser Asp Ile
                435                 440                 445

Ala Val Glu Trp Glu Ser Asn Gly Gln Pro Glu Asn Asn Tyr Lys Thr
                450                 455                 460

Thr Pro Pro Val Leu Asp Ser Asp Gly Ser Phe Phe Leu Tyr Ser Lys
465                 470                 475                 480

Leu Thr Val Asp Lys Ser Arg Trp Gln Gln Gly Asn Val Phe Ser Cys
                485                 490                 495

Ser Val Met His Glu Ala Leu His Asn His Tyr Thr Gln Lys Ser Leu
                500                 505                 510

Ser Leu Ser Pro Gly Lys
                515

<210> SEQ ID NO 4
<211> LENGTH: 357
<212> TYPE: PRT
<213> ORGANISM: Artificial Sequence
<220> FEATURE:
<223> OTHER INFORMATION: Human KIM-1 Partial Extracellular Domain Fc
      Construct
```

<400> SEQUENCE: 4

```
Met His Pro Gln Val Val Ile Leu Ser Leu Ile Leu His Leu Ala Asp
1               5                   10                  15

Ser Val Ala Gly Ser Val Lys Val Gly Gly Glu Ala Gly Pro Ser Val
            20                  25                  30

Thr Leu Pro Cys His Tyr Ser Gly Ala Val Thr Ser Met Cys Trp Asn
        35                  40                  45

Arg Gly Ser Cys Ser Leu Phe Thr Cys Gln Asn Gly Ile Val Trp Thr
    50                  55                  60

Asn Gly Thr His Val Thr Tyr Arg Lys Asp Thr Arg Tyr Lys Leu Leu
65                  70                  75                  80

Gly Asp Leu Ser Arg Arg Asp Val Ser Leu Thr Ile Glu Asn Thr Ala
                85                  90                  95

Val Ser Asp Ser Gly Val Tyr Cys Cys Arg Val Glu His Arg Gly Trp
            100                 105                 110

Phe Asn Asp Met Lys Ile Thr Val Ser Leu Glu Ile Val Pro Pro Lys
        115                 120                 125

Val Val Asp Lys Thr His Thr Cys Pro Pro Cys Pro Ala Pro Glu Leu
    130                 135                 140

Leu Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355
```

<210> SEQ ID NO 5
<211> LENGTH: 8
<212> TYPE: PRT
<213> ORGANISM: Artificial Sequence
<220> FEATURE:
<223> OTHER INFORMATION: C-terminal peptide for Human KIM-1

Extracellular Domain Histag Construct

<400> SEQUENCE: 5

Val Glu His His His His His His
 1               5

<210> SEQ ID NO 6
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 6

Asp Tyr Lys Asp Asp Asp Asp Lys
 1               5

<210> SEQ ID NO 7
<211> LENGTH: 298
<212> TYPE: PRT
<213> ORGANISM: Artificial Sequence
<220> FEATURE:
<223> OTHER INFORMATION: Human KIM-1 Extracellular Domain Histag
      Construct

<400> SEQUENCE: 7

Met His Pro Gln Val Val Ile Leu Ser Leu Ile Leu His Leu Ala Asp
 1               5                  10                  15

Ser Val Ala Gly Ser Val Lys Val Gly Gly Glu Ala Gly Pro Ser Val
             20                  25                  30

Thr Leu Pro Cys His Tyr Ser Gly Ala Val Thr Ser Met Cys Trp Asn
         35                  40                  45

Arg Gly Ser Cys Ser Leu Phe Thr Cys Gln Asn Gly Ile Val Trp Thr
     50                  55                  60

Asn Gly Thr His Val Thr Tyr Arg Lys Asp Thr Arg Tyr Lys Leu Leu
 65                  70                  75                  80

Gly Asp Leu Ser Arg Arg Asp Val Ser Leu Thr Ile Glu Asn Thr Ala
                 85                  90                  95

Val Ser Asp Ser Gly Val Tyr Cys Cys Arg Val Glu His Arg Gly Trp
            100                 105                 110

Phe Asn Asp Met Lys Ile Thr Val Ser Leu Glu Ile Val Pro Pro Lys
        115                 120                 125

Val Thr Thr Thr Pro Ile Val Thr Thr Val Pro Thr Val Thr Thr Val
    130                 135                 140

Arg Thr Ser Thr Thr Val Pro Thr Thr Thr Val Pro Thr Thr Thr
145                 150                 155                 160

Val Pro Thr Thr Met Ser Ile Pro Thr Thr Thr Val Pro Thr Thr
            165                 170                 175

Met Thr Val Ser Thr Thr Thr Ser Val Pro Thr Thr Ser Ile Pro
        180                 185                 190

Thr Thr Thr Ser Val Pro Val Thr Thr Val Ser Thr Phe Val Pro
    195                 200                 205

Pro Met Pro Leu Pro Arg Gln Asn His Glu Pro Val Ala Thr Ser Pro
210                 215                 220

Ser Ser Pro Gln Pro Ala Glu Thr His Pro Thr Thr Leu Gln Gly Ala
225                 230                 235                 240

Ile Arg Arg Glu Pro Thr Ser Ser Pro Leu Tyr Ser Tyr Thr Thr Asp
            245                 250                 255

```
Gly Asn Asp Thr Val Thr Glu Ser Ser Asp Gly Leu Trp Asn Asn Asn
            260                 265                 270

Gln Thr Gln Leu Phe Leu Glu His Ser Leu Leu Thr Ala Asn Thr Thr
        275                 280                 285

Lys Gly Val Glu His His His His His His
    290                 295

<210> SEQ ID NO 8
<211> LENGTH: 1398
<212> TYPE: DNA
<213> ORGANISM: Artificial Sequence
<220> FEATURE:
<223> OTHER INFORMATION: Human KIM-1 Extracellular Domain Fe Construct
      Fc

<400> SEQUENCE: 8
atgaatcaga ttcaagtctt catttcaggc ctcatactgc ttctcccagg cactgtggat      60
tcttatgtgg aagtaaaggg ggtagtgggt caccctgtca cattccatg tacttactca     120 acatatcgtg aatcacaac gacatgttgg ggccgagggc aatgcccatc ttctgcttgt     180
caaaatacac ttatttggac caatggacat cgtgtcacct atcagaagag cagtcggtac     240
aacttaaagg ggcatatttc agaaggagat gtgtccttga cgatagagaa ctctgttgag     300
agtgacagtg gtctgtattg ttgtcgagtg gagattcctg gatggtttaa tgatcagaaa     360 gtgaccttt cattgcaagt taaaccagag attcccacac gtcctccaac aagacccaca     420
actacaaggc ccacagctac aggaagaccc acgactattt caacaagatc acacacatgta   480 ccaacatcaa tcagagtctc tacctccact cctccaacat ctacacacac atggactcac    540
aaaccagaac ccactacatt ttgtccccat gagacaacag ctgaggtgac aggaatccca     600
tcccatactc ctacagactg gaatggcact gcgacatcct caggagatac ctggagtaat     660
cacactgaag caatccctcc agggaagccg cagaaaaacc ctactaaggg cgtcgacaaa    720
actcacacat gcccaccgtg cccagcacct gaactcctgg ggggaccgtc agtcttcctc     780
ttcccccaaa acccaaggga caccctcatg atctcccgga cccctgaggt cacatgcgtg     840
gtggtggacg tgagccacga agaccctgag gtcaagttca actggtacgt ggacggcgtg     900
gaggtgcata atgccaagac aaagccgcgg gaggagcagt acaacagcac gtaccgtgtg     960
gtcagcgtcc tcaccgtcct gcaccaggac tggctgaatg gcaaggagta caagtgcaag    1020
gtctccaaca aagccctccc agcccccatc gagaaaacca tctccaaagc caaagggcag    1080
ccccgagaac cacaggtgta caccctgccc ccatcccggg atgagctgac caagaaccag    1140
gtcagcctga cctgcctggt caaaggcttc tatcccagcg acatcgccgt ggagtgggag    1200
agcaatgggc agccggagaa caactacaag accacgcctc ccgtgttgga ctccgacggc    1260
tccttcttcc tctacagcaa gctcaccgtg gacaagagca ggtggcagca ggggaacgtc    1320
ttctcatgct ccgtgatgca tgaggctctg cacaaccact acacgcagaa gagcctctcc    1380
ctgtctcccg ggaaatga                                                 1398

<210> SEQ ID NO 9
<211> LENGTH: 465
<212> TYPE: PRT
<213> ORGANISM: Artificial Sequence
<220> FEATURE:
<223> OTHER INFORMATION: KIM-1 Fc Fusion

<400> SEQUENCE: 9

Met Asn Gln Ile Gln Val Phe Ile Ser Gly Leu Ile Leu Leu Leu Pro
```

-continued

```
  1               5                   10                  15
Gly Thr Val Asp Ser Tyr Val Glu Val Lys Gly Val Gly His Pro
              20                  25                  30
Val Thr Leu Pro Cys Thr Tyr Ser Thr Tyr Arg Gly Ile Thr Thr Thr
              35                  40                  45
Cys Trp Gly Arg Gly Gln Cys Pro Ser Ser Ala Cys Gln Asn Thr Leu
 50                  55                  60
Ile Trp Thr Asn Gly His Arg Val Thr Tyr Gln Lys Ser Ser Arg Tyr
 65                  70                  75                  80
Asn Leu Lys Gly His Ile Ser Glu Gly Asp Val Ser Leu Thr Ile Glu
              85                  90                  95
Asn Ser Val Glu Ser Asp Ser Gly Leu Tyr Cys Cys Arg Val Glu Ile
             100                 105                 110
Pro Gly Trp Phe Asn Asp Gln Lys Val Thr Phe Ser Leu Gln Val Lys
             115                 120                 125
Pro Glu Ile Pro Thr Arg Pro Thr Arg Pro Thr Thr Thr Arg Pro
             130                 135                 140
Thr Ala Thr Gly Arg Pro Thr Thr Ile Ser Thr Arg Ser Thr His Val
145                 150                 155                 160
Pro Thr Ser Ile Arg Val Ser Thr Ser Thr Pro Pro Thr Ser Thr His
             165                 170                 175
Thr Trp Thr His Lys Pro Glu Pro Thr Thr Phe Cys Pro His Glu Thr
             180                 185                 190
Thr Ala Glu Val Thr Gly Ile Pro Ser His Thr Pro Thr Asp Trp Asn
             195                 200                 205
Gly Thr Ala Thr Ser Ser Gly Asp Thr Trp Ser Asn His Thr Glu Ala
210                 215                 220
Ile Pro Pro Gly Lys Pro Gln Lys Asn Pro Thr Lys Gly Val Asp Lys
225                 230                 235                 240
Thr His Thr Cys Pro Pro Cys Pro Ala Pro Glu Leu Leu Gly Gly Pro
             245                 250                 255
Ser Val Phe Leu Phe Pro Pro Lys Pro Lys Asp Thr Leu Met Ile Ser
             260                 265                 270
Arg Thr Pro Glu Val Thr Cys Val Val Val Asp Val Ser His Glu Asp
             275                 280                 285
Pro Glu Val Lys Phe Asn Trp Tyr Val Asp Gly Val Glu Val His Asn
             290                 295                 300
Ala Lys Thr Lys Pro Arg Glu Glu Gln Tyr Asn Ser Thr Tyr Arg Val
305                 310                 315                 320
Val Ser Val Leu Thr Val Leu His Gln Asp Trp Leu Asn Gly Lys Glu
             325                 330                 335
Tyr Lys Cys Lys Val Ser Asn Lys Ala Leu Pro Ala Pro Ile Glu Lys
             340                 345                 350
Thr Ile Ser Lys Ala Lys Gly Gln Pro Arg Glu Pro Gln Val Tyr Thr
             355                 360                 365
Leu Pro Pro Ser Arg Asp Glu Leu Thr Lys Asn Gln Val Ser Leu Thr
             370                 375                 380
Cys Leu Val Lys Gly Phe Tyr Pro Ser Asp Ile Ala Val Glu Trp Glu
385                 390                 395                 400
Ser Asn Gly Gln Pro Glu Asn Asn Tyr Lys Thr Thr Pro Pro Val Leu
             405                 410                 415
Asp Ser Asp Gly Ser Phe Phe Leu Tyr Ser Lys Leu Thr Val Asp Lys
             420                 425                 430
```

```
Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
        450                 455                 460

Lys
465
```

US 7,597,887 B2

KIM-1 ANTAGONISTS AND USE TO MODULATE IMMUNE SYSTEM

CROSS REFERENCE TO RELATED APPLICATIONS

This application is a national phase filing under 35 U.S.C. § 371 of international application number PCT/US2003/041294, filed Dec. 29, 2003, which claims the benefit of priority of U.S. provisional application No. 60/436,934, filed Dec. 30, 2002. The disclosures of the prior applications are considered part of (and are incorporated by reference in) the disclosure of this application.

FIELD OF THE INVENTION

The field of the invention is medicine, immunology, molecular biology and protein chemistry.

BACKGROUND OF THE INVENTION

KIM-1 (Kidney Injury Molecule-1) is a type I cell membrane glycoprotein (Ichimura et al., 1998, *J. Biol. Chem.* 273:4135-4142). The extracellular portion (ectodomain) of KIM-1 contains a six-cysteine immunoglobulin-like domain and a T/SP rich domain characteristic of mucin-like O-glycosylated proteins. The mucin domain extends the Ig-like domain away from the cell surface like a stalk (Jentoft, 1990, *Trends Biochem. Sci.* 15:291-294). KIM-1 has been identified as the receptor for hepatitis A virus Kaplan et al., 1996, EMBO J. 15:4282-4296; WO 96/04376; U.S. Pat. No. 5,622,861). Two human KIM-1 splice variants have been discovered, with one being predominant in the liver (Feigelstock, 1998, *J. Virol.* 72:6621-6628), and the other being predominant in the kidney (Ichimura et al., supra).

KIM-1 is a member of a gene family known as the TIM (T cell Immunoglobulin and Mucin domain) family. In addition to KIM-1, there are at least two other members of the TIM family in humans. One member was cloned and originally designated the "200 gene" (WO200073498), but subsequently came to be known as TIM-3. Another member was cloned and designated "gene 58" (WO99/38881).

KIM-1 has attracted interest as a clinical diagnostic marker for kidney damage (Bailly et al., 2002, *J. Biol. Chem.* 277: 39739-39748; Han et al., 2002, *Kidney Intl.* 62:237-244). A mouse homolog of KIM-1 (TIM-1) has been reported to exist within a genetic locus thought to be involved in the development of airway hyperreactivity (McIntire et al., 2001, *Nature Immunology* 2:1109). A mouse protein known as TIM-2 has been reported to play a role in the in vivo generation of antigen-specific T cells (Kumanogoh et al., 2002, *Nature* 419:629-633). A mouse protein known as TIM-3 has been associated with immune response regulation in mice (Monney et al., 2002. *Nature* 415:536-541).

SUMMARY OF THE INVENTION

It has been discovered that treatment of a Mammal with a KIM-1 antagonist alters the interaction of T cells with other immune system cells, e.g., dendritic cells, monocytes macrophages, and B cells, and thereby strongly suppresses an IgG response to an antigen. In addition, it has been discovered that such treatment almost eliminates IgG1 production by memory B cells in response to subsequent challenge with the antigen. In addition, it has been discovered that blockade of the binding of KIM-1 to its receptor reduces secretion of IFN-γ by immune cells engaged in an antigen response in the mixed lymphocyte response (MLR) assay. Based on these discoveries, the invention provides methods for therapeutically modulating immune function in autoimmune diseases and other disorders of the mammalian immune system.

The invention provides a method of inhibiting signaling between a T cell and a second cell, e.g., an antigen-presenting cell (APC), in a mammal. The method includes identifying a mammal, e.g., one with an immune disease or disorder, or one preparing to receive a tissue graft; and administering to the mammal an effective amount of one of the following types of KIM-1 antagonist: (a) a polypeptide comprising a KIM-1 Ig domain, and lacking a transmembrane domain and a KIM-1 cytoplasmic domain; (b) an anti-KIM-1 antibody; and (c) an antigen-binding fragment of an anti-KIM-1 antibody.

The T cell may be an activated T cell, e.g., a T helper cell. It can be a Th2 cell or a Th1 cell. In some embodiments of the invention the T cell is a grafted, donor T cell. The APC can be, but is not limited to, a monocyte, a macrophage, a dendritic cell, or a B cell. In some embodiments of the invention, the APC is presenting an autoantigen.

Preferably, the KIM-1 antagonist is a soluble polypeptide, which can include a KIM-1 mucin domain in addition to the KIM-1 Ig domain. In some embodiments the polypeptide includes a heterologous moiety, e.g., an immunoglobulin (Ig) moiety, a serum albumin moiety, a targeting moiety, a reporter moiety, a multimerization moiety, and a purification-facilitating moiety. A preferred heterologous moiety is an Ig moiety such as an Fc moiety.

In some embodiments the KIM-1 antagonist is a polypeptide conjugated to a polymer such as polyalkylene glycol, a sugar polymer, or a polypeptide. A preferred polymer is a polyalkylene glycol, with polyethylene glycol (PEG) being particularly preferred. The average molecular weight of the polymer preferably is from 2,000 Da to 30,000 Da., and more preferably from 5,000 Da to 20,000 Da., e.g., about 10,000 Da.

The invention provides a method of inhibiting activation of a B cell in a mammal, e.g., by an activated T cell such as a Th2 cell. The method includes contacting the B cell or other APC with an effective amount of a KIM-1 antagonist, or the T cell, if the antagonist is an anti-KIM-1 antibody. In some embodiments of the invention, the activated T cell is a grafted, donor T cell.

The invention provides a method of inhibiting production in a mammal of a subset of antibodies such as IgG, e.g., IgG1, reactive against one or more antigens. The method includes administering an effective amount of a KIM-1 antagonist. In some embodiments the effective amount of the KIM-1 antagonist is administered between 30 minutes and 30 days before the immune system of the mammal first recognizes the one or more antigens. The antigens are alloantigens or autoantigens, depending on the disease, disorder or condition being treated.

The invention provides a method of inhibiting disease relapse in an autoimmune disease. The method includes administering an effective amount of a KIM-1 antagonist.

The invention provides a method of inhibiting epitope spreading in an autoimmune disease. The method includes administering an effective amount of a KIM-1 antagonist.

The invention provides a method of treating a Th2 cell-mediated disease, e.g., systematic lupus erythromatosis, myasthenia gravis, autoimmune hemolytic anemia, Chagas disease, Graves disease, idiopathic thrombocytopenia purpura (ITP), Wegener's granulomatosis, polyarteritis, nodosa, rapidly progressive crescentic glomerulonephritis, or graft-versus-host disease (GVHD), asthma, atopic dermatitis, atopy disorders such as airway hyperresponsive diseases and airway distress syndromes. The method includes administering an effective amount of a KIM-1 antagonist.

The invention provides a method of inhibiting GVHD. The method includes administering an effective amount of a KIM-1 antagonist between 30 minutes and 30 days before the graft.

The invention provides a method of inhibiting secretion of IFN-γ by lymphocytes in a mammal. The method includes administering to the mammal an effective amount of a KIM-1 antagonist.

The invention provides a method of inhibiting the activation of Th1 T cell effector function, and therefore cellular immune responses that occur in inflammatory situations. An example of such an inflammatory situation is inflammatory bowel disease. The method includes administering to the mammal an effective amount of a KIM-1 antagonist.

The invention provides a method of treating an inflammatory disease or disorder in a mammal, e.g., inflammatory bowel diseases such as Crohn's disease, ulcerative colitis, and ileitis. The method includes administering to the mammal an effective amount of a KIM-1 antagonist.

As used herein, "anti-KIM-1 antibody" means an antibody, e.g., an IgG molecule, that binds specifically to the extracellular portion of a full length KIM-1 polypeptide.

As used herein, "full length human KIM-1 polypeptide" means the polypeptide of SEQ ID NO:1 in its entirety or SEQ ID NO:2 in its entirety. These two polypeptides represent splice variants of the human KIM-1 gene.

As used herein, "heterologous moiety" means an amino acid sequence not present in a full-length KIM-1 polypeptide.

As used herein, "KIM-1 antagonist" means (a) a polypeptide comprising a KIM-1 Ig domain, and lacking a transmembrane domain and a KIM-1 cytoplasmic domain; (b) an anti-KIM-1 antibody; or (c) an antigen-binding fragment of an anti-K-1 antibody, each of which blocks, inhibits, or interferes with the biological activity of a naturally-occurring KIM-1.

As used herein, "KIM-1 fusion protein" means a fusion protein that includes a KIM-1 moiety fused to a heterologous moiety.

As used herein, "KIM-1 moiety" means a biologically active fragment of a full-length KIM-1 polypeptide.

As used herein, "KIM-1 polypeptide" means a KIM-1 moiety alone or a fusion protein that includes a KIM-1 moiety.

As used herein, "KIM-1 Ig domain" means a portion of SEQ ID NO:1 whose amino terminus is amino acid 29-36, and whose carboxy terminus is amino acid 105-107.

As used herein, "KIM-1 mucin domain" means a portion of SEQ ID NO:1 whose amino terminus is amino acid 126-130, and whose carboxy terminus is amino acid 255-274.

As used herein, "KIM-1 transmembrane domain" means amino acids 290-311 of SEQ ID NO:1.

As used herein, "KIM-1 cytoplasmic domain" means amino acids 312-334 of SEQ ID NO:2, or 312-359 of SEQ ID NO:1.

Unless otherwise defined, all technical and scientific terms used herein have the same meaning as commonly understood by one of ordinary skill in the art to which the invention pertains. In case of conflict, the present specification, including definitions, will control. All publications, patents and other references mentioned herein are incorporated by reference.

Although methods and materials similar or equivalent to those described herein can be used in the practice or testing of the invention, the preferred methods and materials are described below. The materials, methods and examples are illustrative only, and are not intended to be limiting. Other features and advantages of the invention will be apparent from the detailed description and from the claims.

BRIEF DESCRIPTION OF THE DRAWINGS

FIG. 1 (prior art) is a schematic representation of two naturally-occurring splice variants of the human KIM-1 polypeptide (top variant is SEQ ID NO:2; bottom variant is SEQ ID NO:1). The two amino acid sequences are identical through residue 323. The signal sequence (residues 1-20) is indicated by an underline. The transmembrane domain (residues 290-311) is indicated by a double underline.

FIG. 2 (prior art) is a schematic representation of the 359-amino acid human KIM-1 splice variant. The signal sequence and transmembrane domains are indicated by dark shading. Cysteine residues in the Ig domain are indicated by "C." Inverted triangles indicated N-glycan attachment points. A TSP-rich region, which corresponds to the mucin domain, is indicated by shaded thickening.

DETAILED DESCRIPTION OF THE INVENTION

Figure 3:
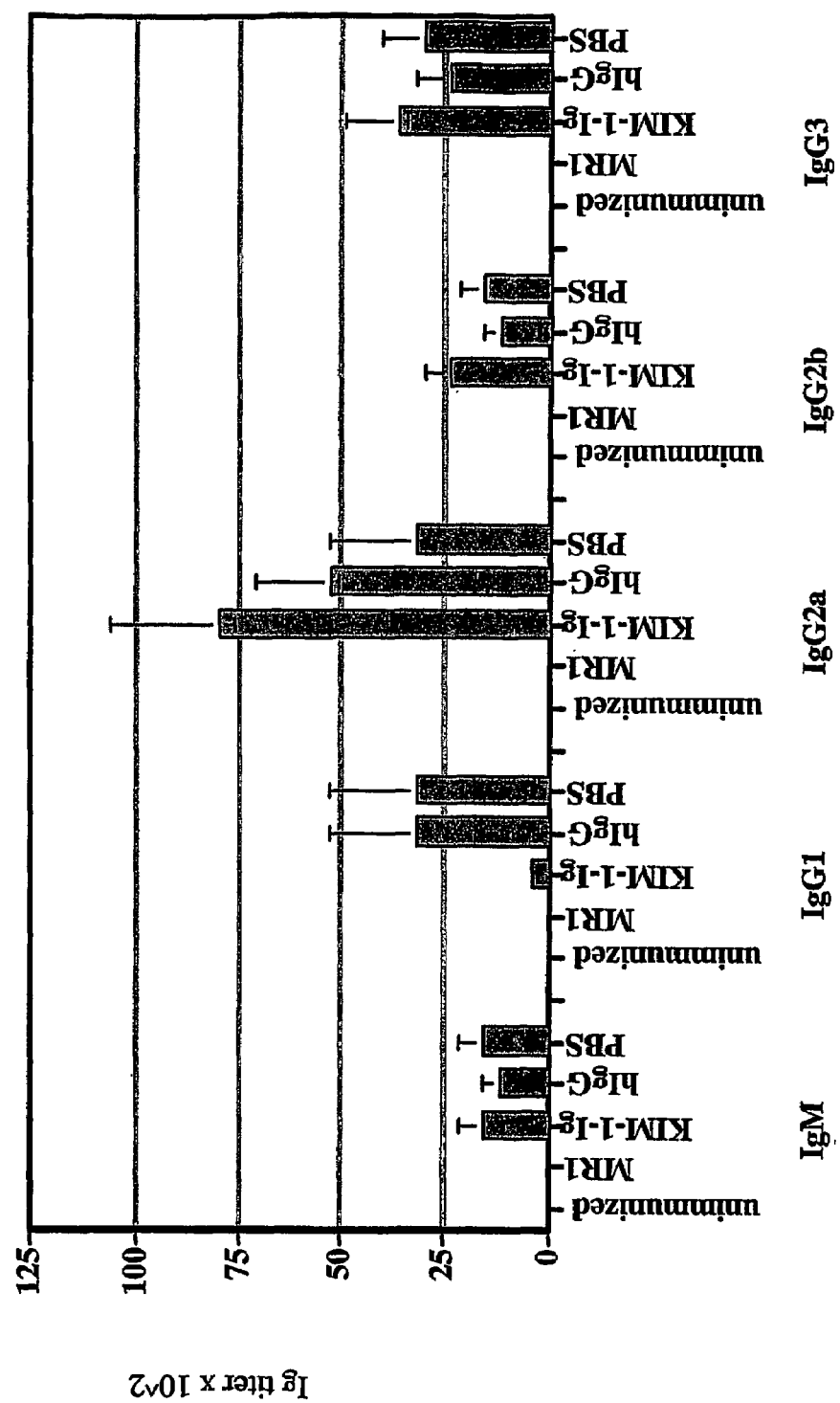
FIG. 3 is a histogram summarizing immunoglobulin titers measured on day 14 in Balb/c mice receiving a primary challenge with sheep red blood cells (experiment 1).

The native human KIM-1 gene encodes a polypeptide (FIG. 1) containing 334 amino acids or 359 amino acids (SEQ ID NOs:2 or 1, respectively), depending on splice variation, which is at least partially tissue-dependent. Both sequences include: a signal sequence, an Ig domain, a mucin domain, a transmembrane domain, and a cytoplasmic domain.

Using a soluble, dimerized, KIM-1 ectodomain-Fc fusion protein (each monomer containing the mouse KIM-1 ectodomain and a human Fc moiety) and a recognized animal model (murine SRBC response), the inventors have achieved a profound alteration of the mammalian immune response. Without intending to be bound by theory, the inventors interpret the observed results as indicating that the fusion protein acts as a KIM-1 antagonist, and that this antagonism interferes with a KIM-1-mediated signaling interaction between T cells and APCs. The downstream effects of this interference include useful modulation of the mammalian immune response. Such modulation can be used to treat autoimmune diseases and other diseases and disorders in which a mammalian immune system attacks an inappropriate target, either through T cell cytotoxicity or through an immunoglobulin response. Examples of diseases or disorders in which immune system modulation would be beneficial include, but are not limited to, arthritis, systemic lupus erythromatosis (also known as SLE or lupus), and graft-versus-host-disease (GVHD).

In methods of the present invention, a soluble KIM-1 antagonist polypeptide or a KIM-1 blocking antibody (or antigen-binding antibody fragment) can be administered directly as a pre-formed polypeptide. Alternatively, it can be administered indirectly through a nucleic acid vector (encoding and expressing the polypeptide). Either way, the result is to antagonize KIM-1-mediated effects on T cells, including T cell activation and stimulation of T cell proliferation. This antagonism of KIM-1 located on T cells can achieve a desired therapeutic effect directly by blocking destructive actions of the T cells themselves. In addition, the antagonism can achieve the desired therapeutic effect indirectly, by blocking activated T cell-mediated activation of B cells, thereby reducing deleterious antibody production.

In various diseases, including autoimmune diseases and certain types of pathogenic infections, damage results from autoantibody responses, i.e., production of antibodies that recognize self-antigens. The present invention provides methods and molecules for reducing such damage by interfering with T cell activation and differentiation. This, in turn, interferes with activated T cell-mediated B cell activation, which interferes with production and secretion of specific immunoglobulins, e.g., IgG1, by the B cells. Accordingly, any disease or disorder characterized by autoantibody responses can be treated by using methods and molecules of the invention.

When certain autoimmune diseases are being treated, exposure to antigens, and the immune system responses, are transient. This results in remissions during which administration of an effective amount of a KIM-1 antagonist would inhibit subsequent reactivation of the immune responses to one or more antigens. In this way the invention can be used to block disease relapse. When certain autoimmune diseases are being treated, the immune system of the mammal first recognizes the one or more antigens as part of an epitope spreading process in the course of an autoimmune disease.

Much of the damage in graft-versus-host disease (GVHD) results directly from actions of donor T cells that become activated in the host (in response to host antigens), once grafted, e.g., in a bone marrow transplant. By virtue of its ability to interfere with T cell activation, the present invention is useful for inhibiting GVHD. In addition to damage from direct actions of activated donor T cells, there is also an antibody-mediated component in GVHD. Because this antibody-mediated component depends on activation of donor T cells, which activate the autoantibody-producing B cells, the invention reduces autoantibody-mediated damage, as well as cellular immunity-mediated damage in GVHD.

Antibody-Mediated Autoimmune Diseases

Systematic lupus erythromatosis (SLE; lupus) is a TH-2 mediated autoimmune disorder characterised by high levels of autoantibodies directed against intracellular antigens such as double stranded DNA, single stranded DNA, and histones. In view of these characteristics, lupus exemplifies an autoimmune disease that can be treated according to the present invention.

Examples of other organ-specific or systemic autoimmune diseases suitable for treatment according to the invention include myasthenia gravis, autoimmune hemolytic anemia, Chagas' disease, Graves disease, idiopathic thrombocytopenia purpura (ITP), Wegener's Granulomatosis, poly-arteritis Nodosa and Rapidly Progressive Crescentic Glomerulonephritis. See, e.g., Benjamini et al., 1996, *Immunology, A Short Course, Third Ed.* (Wiley-Liss, New York). In addition, rheumatoid arthritis (RA), once thought to be mediated by T cell cytotoxic activity, is now known to have a B cell and/or antibody component (Leandro et al., 2002, *Ann. Rheum. Dis.*, 61:863-866; De Vita et al., *Arthritis Rheum.* 46:2029-2033; Tsuji et al., 2002, *J. Exp. Med.* 196:1277-1290), and thus is suitable for treatment according to the invention.

The normal immune response to some pathogenic infectious agents elicits deleterious autoantibody responses. One example is Chagas' disease, an inflammatory cardiomyopathy that develops in humans and experimental animals chronically infected with *Trypanosoma cruzi*. Anti self antibodies occur in the sera of Chagas' disease patients (Bach-Elias et al., 1998, *Parasitol. Res.* 84:796-799; Tibbetts, et al., 1994, *J. Immunol.* 152:1493-1499), and thus this disease is suitable for treatment according to the invention.

Another example of cell destruction by autoantibodies resulting from infection is idiopathic thrombocytopenia purpura (ITP), in which autoantibodies cause platelet destruction (by complement or phagocytic cells with. Fc or C3b receptor) and can lead to bleeding. ITP is suitable for treatment according to the invention.

Graft-Versus Host Disease (GVHD)

GVHD exemplifies a T cell-mediated condition that can be treated using methods of the invention. GVHD is initiated when donor T cells recognize host antigens as foreign. GVHD, often a fatal consequence of bone marrow transplantation (BMT) in human patients, can be acute or chronic. Acute and chronic forms of GVHD exemplify the development of antigen specific Th1 and Th2 responses, respectively. Acute GVHD occurs within the first 2 months following BMT, and is characterized by donor cytotoxic T cell-mediated damage to skin, gut, liver, and other organs. Chronic GVHD appears later (over 100 days post-BMT) and is characterized by hyperproduction of immunoglobulin (Ig), including autoantibodies, and damage to the skin, kidney, and other organs caused by Ig-deposition. Nearly 90% of acute GVHD patients go on to develop chronic GVHD. Chronic GVHD appears to be a Th2 T cell mediated disease (De Wit et al., 1993, *J. Immunol.* 150:361-366). Acute GVHD is a Th1 mediated disease (Krenger et al., 1996, *Immunol. Res.* 15:50-73; Williamson et al., 1996, *J. Immunol.* 157:689-699). T cell cytotoxicity is a characteristic of acute GVHD. The consequence of donor anti-host cytotoxicity can be seen in various ways. First, host lymphocytes are rapidly destroyed, such that mice experiencing acute GVHD are profoundly immunosuppressed. Second, donor lymphocytes become engrafted and expand in the host spleen, and their cytotoxic activity can be directly measured in vitro by taking advantage of cell lines that express the host antigens that can be recognized (as foreign) by the donor cells. Third, the disease becomes lethal as additional tissues and cell populations are destroyed.

Chronic GVHD results from antibody-mediated destruction of host tissues and cells and has been called "SLE-like" GVHD. Manifestations include autoantibody formation, Ig-deposition in various organs (kidney, liver), skin rash, lymphoid hyperplasia, Sjögren-like lesions, scleroderma-like lesions, polyarteritis, and other pathologies. This disease is partly mediated by autoantibody formation. In view of the foregoing, chronic GVHD is suitable for treatment according to the invention.

Other Th2-Related Diseases

Atopic disorders are characterized by the expression by immune system cells, including activated T cells and APC, of cytokines, chemokines, and other molecules which are characteristic of Th2 responses, such as the IL-4, IL-5 and IL-13 cytokines, among others. Such atopic disorders therefore will be amenable to treatment by methods that antagonize the development of the Th2 response, such as the KIM-1 antagonists of the invention, Atopic disorders include asthma, the airway hypersensitivity and distress syndromes, and pathologies such as atopic dermatitis. The invention provides a method of inhibiting atopic disorders. The method includes administering an effective amount of a KIM-1 antagonist.

Inflammatory Diseases and Disorders Mediated by Activated Lymphocytes, APC and Pro-Inflammatory Cytokines Using the mixed lymphocyte reaction assay (MLR) in the mouse and human model systems, the inventors have shown that blockade of KIM-1 binding to its receptor, e.g., using anti-KIM-1 mAbs or a KIM-1-Ig fusion protein, reduces the secretion of IFNγ by responder cells. Accordingly, a KIM-1 antagonist can be used to treat any disease or disorder mediated by IFNγ.

IFNγ is a critical cytokine in immune responses. It has pleotropic effects on the development and extent of inflammatory and immune processes (Boehm et al. 1997, *Ann Rev Immunol* 15:749-795). Deficiencies in IFNγ production reduce anti-viral and anti-bacterial responses and attenuate inflammatory responses. A KIM-1 antagonist can be used advantageously to reduce IFNγ production in diseases or disorders where IFNγ production is excessive or inappropriate. Examples of such diseases or disorders include autoimmune diseases, colitis and chronic inflammation.

IFNγ is a key component of T cell activation and B cell responses. It influences T cell effector cell development (e.g., via cross regulation with Il-4) and B cell activation (e.g., via regulation of MHC-mediated antigen presentation and expression of B7 molecules). IFNγ is a critical component of Th1 T cell-mediated immune responses. IFNγ has pronounced effects on other immune system components such as macrophages and neutrophils. It stimulates their activation and release of toxic effector molecules.

IFNγ has potent effects on tissue resident cell types. Endothelium is activated by IFNγ. When stimulated with IFNγ, resident cells in diseased tissue, e.g., synoviocytes in rheumatoid arthritis, secrete TNF and other cytokines, MCP-1 and other chemokines, and toxic effector molecules such as nitric oxide. All of these latter functions mediated by IFNγ influence cell trafficking into tissues during inflammation.

As shown in Example 5 (below), blockade of KIM-1 binding to its receptor reduces or eliminates IgG1 production in the SRBC model system. In the MLR assay, the inventor has found that blockade of KIM-1 binding to its receptor reduces IFNγ production by lymphocytes. Without intending to be bound by theory, it is noted that the reduction in IgG1 production and the reduction in IFNγ production may represent two separate effects of KIM-1 blockade, and may not directly related. Therefore, when a KIM-1 antagonist is used to modulate immune function according to the invention, the KIM-1 antagonist may provide a beneficial effect through two separate mechanisms of action.

Fusion Proteins and Conjugated Polypeptides

Some embodiments of the invention involve a KIM-1 antagonist polypeptide wherein a KIM-1 moiety is fused to a heterologous moiety to form a KIM-1 fusion protein. KIM-1 fusion proteins, as opposed to a KIM-1 moiety alone, can be used to accomplish various objectives. Such objectives include, for example, increased serum half-life, improved bioavailability, in vivo targeting to a specific organ or tissue type, improved recombinant expression efficiency, improved host cell secretion, and ease of purification. Depending on the objective(s) to be achieved, the heterologous moiety can be inert or biologically active. Also, it can be chosen to be stably fused to the KIM-1 moiety or to be cleavable, in vitro or in vivo. Heterologous moieties to accomplish different objectives are known in the art.

As an alternative to expression of a KIM-1 fusion protein, a chosen heterologous moiety can be preformed and chemically conjugated to the KIM-1 moiety. In most cases, a chosen heterologous moiety will function similarly, whether fused or conjugated to the KIM-1 moiety. Therefore, in the following discussion of heterologous amino acid sequences, unless otherwise noted, it is to be understood that the heterologous sequence can be joined to the KIM-1 moiety in the form of a fusion protein or as a chemical conjugate.

Pharmacologically active polypeptides such as a KIM-1 polypeptide often exhibit rapid in vivo clearance, necessitating large doses to achieve therapeutically effective concentrations in the body. In addition, polypeptides smaller than about 20 kDa potentially undergo glomerular filtration, which sometimes leads to nephrotoxicity. Fusion or conjugation of relatively small polypeptides such as KIM-1 fragments can be employed to reduce or avoid the risk of such nephrotoxicity. Various heterologous amino acid sequences, i.e., polypeptide moieties or "carriers," for increasing the in vivo stability, i.e., serum half-life, of therapeutic polypeptides are known.

Due to its long half-life, wide in vivo distribution, and lack of enzymatic or immunological function, essentially full-length human serum albumin (HSA), or an HSA fragment, is a preferred heterologous moiety. Through application of methods and materials such as those taught in Yeh et al., 1992, *Proc. Natl. Acad. Sci. USA,* 89:1904-1908 and Syed et al., 1997, *Blood* 89:3243-3252, HSA can be used to form a KIM-1 fusion protein or conjugate that displays pharmacological activity by virtue of the KIM-1 moiety while displaying significantly increased, e.g., 10-fold to 100-fold higher, in vivo stability. Preferably, the N-terminus of the HSA is fused to the C-terminus of the KIM-1 moiety. Since HSA is a naturally secreted protein, the HSA signal sequence can be exploited to obtain secretion of the KIM-1 fusion protein into the cell culture medium, when the fusion protein is produced in a eukaryotic, e.g., mammalian, expression system.

Some embodiments of the invention employ a KIM-1 polypeptide wherein a KIM-1 moiety is fused to an Fc region, i.e., the C-terminal portion of an Ig heavy chain constant region. Potential advantages of a KIM-1-Fc fusion include solubility, in vivo stability, and multivalency, e.g., dimerization. The Fc region used can be an IgA, IgD, or IgG Fc region (hinge-CH2-CH3). Alternatively, it can be an IgE or IgM Fc region (hinge-CH2-CH3-CH4). An IgG Fc region is preferred, e.g., an IgG1 Fc region or IgG4 Fc region. Materials and methods for constructing and expressing DNA encoding Fc fusions are known in the art and can be applied to obtain KIM-1 fusions without undue experimentation.

Preferably, the KIM-1-Fc fusion is constructed with an orientation wherein the KIM-1 moiety forms the amino-terminal portion of the fusion protein. For an example of construction and expression of an Fc fusion with this orientation, see, e.g., Wallner et al., U.S. Pat. No. 5,547,853 (pSAB152). Alternatively, the fusion can be constructed with the opposite orientation, i.e., wherein the KIM-1 moiety forms the carboxy-terminal portion of the fusion. For examples and discussion of this orientation, see, e.g., Lo et al., U.S. Pat. No. 5,541,087.

Some embodiments of the invention employ a KIM-1 fusion protein obtained by constructing a KIM-1 immunofusin DNA in accordance with Lo et al., U.S. Pat. No. 5,541, 087. An immunofusin DNA includes a polynucleotide encoding a secretion cassette. The secretion cassette includes sequences encoding (in the 5' to 3' direction) a signal sequence, an immunoglobulin Fc region, and a KIM-1 moiety fused to the 3' end of the secretion cassette. DNA can be expressed at high levels in a host cell, and the fusion protein is efficiently produced and secreted from the host cell. The secreted immunofusin can be collected from the culture media without the need for lysis of the host cell.

In some embodiments the DNA sequence encodes a proteolytic cleavage site between the KIM-1 moiety and the heterologous moiety. A cleavage site provides for the proteolytic cleavage of the encoded fusion protein, thus separating the Fc domain from the target protein. Useful proteolytic cleavage sites include amino acids sequences recognized by proteolytic enzymes such as trypsin, plasmin or enterokinase K.

A KIM-1 polypeptide construct can be incorporated into a replicable expression vector. Useful vectors include linear nucleic acids, plasmids, phagemids, cosmids and the like. An exemplary expression vector is pSAB152 (Wallner et al., U.S. Pat. No. 5,547,853. Another exemplary expression vector is pdC, in which the transcription of the immunofusin DNA is placed under the control of the enhancer and promoter of the human cytomegalovirus (Lo et al., 1991, *Biochim. Biophys. Acta* 1088:712; and Lo et al., 1998, *Protein Engineering* 11:495-500). An appropriate host cell can be transformed or transfected with a DNA that encodes a KIM-1 polypeptide, and is used for the expression and secretion of the KIM-1 polypeptide. Preferred host cells include immortal hybridoma cells, myeloma cells, 293 cells, Chinese hamster ovary (CHO) cells, Hela cells, and COS cells.

Fully intact, wild type Fc regions display effector functions that normally are unnecessary and undesired in an Fc fusion protein according to the present invention. Therefore, certain binding sites preferably are deleted from the Fc region during the construction of a KIM-1-Fc fusion protein. For example, since coexpression with the light chain is unnecessary, the binding site for the heavy chain binding protein, Bip (Hendershot et al., 1987, *Immunol. Today* 8:111-114), is deleted from the Fc region of IgE, such that this site does not interfere with the efficient secretion of the fusion protein. Likewise, the cysteine residues present in the Fc regions which are responsible for binding to the light chain of the immunoglobulin should be deleted or substituted with another amino acid, such that these cysteine residues do not interfere with the proper folding of the Fc region when it is produced as an immunofusin. Transmembrane domain sequences, such as those present in IgM, should be deleted.

The IgG1 Fc region is preferred. Alternatively, the Fc region of the other subclasses of immunoglobulin gamma (gamma-2, gamma-3 and gamma-4) can be used in the secretion cassette. The IgG1 Fc region of immunoglobulin gamma-1 that is preferably used in the secretion cassette includes the hinge region (at least part), the CH2 region, and the CH3 region. In some embodiments, the Fc region of immunoglobulin gamma-1 is a CH2-deleted-Fc, which includes part of the hinge region and the CH3 region, but not the CH2 region. A CH2-deleted-Fc has been described by Gillies et al., 1990, *Hum. Antibod. Hybridomas,* 1:47. In some embodiments, the Fc regions of IgA, IgD, IgE, or IgM, are used.

KIM-1-Fc fusion proteins can be constructed in several different configurations. In one configuration the C-terminus of the KIM-1 moiety is fused directly to the N-terminus of the Fc moiety. In a slightly different configuration, a short linker, e.g., 2-10 amino acids, is incorporated into the fusion between the C-terminus of the KIM-1 moiety and the N-terminus of the Fc moiety. Such a linker provides conformational flexibility, which may improve biological activity in some circumstances. If a sufficient portion of the hinge region is retained in the Fc moiety, the KIM-1-Fc fusion will dimerize, thus forming a divalent molecule. A homogeneous population of monomeric Fc fusions will yield monospecific, bivalent dimers. A mixture of two monomeric Fc fusions each having a different specificity will yield bispecific, bivalent dimers.

KIM-1 conjugates can be constructed using methods known in the art. Any of a number of cross-linkers that contain a corresponding amino reactive group and thiol reactive group can be used to link KIM-1 to serum albumin. Examples of suitable linkers include amine reactive cross-linkers that insert a thiol reactive-maleimide. These include, e.g., SMCC, AMAS, BMPS, MBS, EMCS, SMPB, SMPH, KMUS, or GMBS. Other suitable linkers insert a thiol reactive-haloacetate group. These include, e.g., SBAP, SIA, SLAB and that provide a protected or non protected thiol for reaction with sulfhydryl groups to product a reducible linkage are SPDP, SMPT, SATA, or SATP all of which are commercially available (e.g., Pierce Chemicals). One skilled in the art can similarly envision with alternative strategies that will link the N-terminus of KIM-1 with serum albumin.

One skilled in the art can generate conjugates to serum albumin that are not targeted at the N-terminus of a KIM-1 polypeptide or at the thiol moiety on serum albumin. For example KIM-1-albumin fusions can be generated using genetic engineering techniques, wherein the KIM-1 moiety is fused to the serum albumin gene at its amino-terminus (N-ter), carboxy-terminus (C-ter), or at both ends.

Other derivatives of KIM-1 polypeptides include covalent or aggregate conjugates of modified KIM-1 or its fragments with other proteins or polypeptides, such as by synthesis in recombinant culture as additional N-termini, or C termini. For example, the conjugated peptide may be a signal (or leader) polypeptide sequence at the N-terminal region of the protein which co-translationally or post-translationally directs transfer of the protein from its site of synthesis to its site of function inside or outside of the cell membrane or wall (e.g., the yeast alpha-factor leader). KIM-1 polypeptides can be fused to heterologous peptides to facilitate purification or identification of the KIM-1 moiety (e.g., histidine/KIM-1 fusions). The KIM-1 moiety also can be linked to the peptide Asp-Tyr-Lys-Asp-Asp-Asp-Asp-Lys (DYKDDDDK) (SEQ ID NO:6) (Hopp et al., 1988, *Biotechnology* 6:1204). This sequence is highly antigenic and provides an epitope reversibly bound by a specific monoclonal antibody. Consequently, it facilitates assay and purification of the expressed recombinant protein. This sequence is specifically cleaved by bovine mucosal enterokinase at the residue immediately following the Asp-Lys pairing.

Expression systems employing gene fusion constructs have been used to enhance the production of proteins in bacteria. Employing a bacterial protein that is normally expressed at a very high level as the amino-terminal fusion partner of a fusion protein helps to ensure efficient transcription and translation of the message, and in some cases the secretion and solubilization of the fusion protein (Smith et al., 1988 *Gene* 67:31; Hopp et al., supra; La Vallie et al., 1993, *Biotechnology* 11:187).

Conjugated Polymers (Other Than Polypeptides)

Some embodiments of the invention involve a KIM-1 polypeptide wherein one or more polymers are conjugated (covalently linked) to the KIM-1 polypeptide. Examples of polymers suitable for such conjugation include polypeptides (discussed above), sugar polymers and polyalkylene glycol chains. Typically, but not necessarily, a polymer is conjugated to the KIM-1 polypeptide for the purpose of improving one or more of the following: solubility, stability, or bioavailability.

A preferred class of polymer for conjugation to a KIM-1 polypeptide is a polyalkylene glycol. Polyethylene glycol (PEG) is a preferred polyalkylene glycol. PEG moieties, e.g., 1-6 PEG polymers, can be conjugated to each KIM-1 polypeptide to increase serum half life, as compared to the KIM-1 polypeptide alone. PEG moieties are non-antigenic and essentially biologically inert. PEG moieties used in the practice of the invention may be branched or unbranched.

The number of PEG moieties attached to the KIM-1 polypeptide and the molecular weight of the individual PEG chains can vary. In general, the higher the molecular weight of the polymer, the fewer polymer chains attached to the polypeptide. Preferably, the average molecular weight of PEG is from 2 kDa to 100 kDa. More preferably, the average molecular weight is from 5 Da to 20 kDa, with 8-12 kDa being most preferred.

The polymer, e.g., PEG, can be linked to the KIM-1 polypeptide through any suitable, exposed reactive group on the polypeptide. The exposed reactive group(s) can be, for example, an N-terminal amino group or the epsilon amino group of an internal lysine residue, or both. Naturally-occurring lysine residues can be exploited for this purpose, or lysine residue(s) can be engineered into the KIM-1 amino acid sequence. An activated polymer can react and covalently link at any free amino group on the KIM-1 polypeptide. Free carboxylic groups, suitably activated carbonyl groups, hydroxyl, guanidyl, imidazole, oxidized carbohydrate moieties and mercapto groups of the KIM-1 (if available) also can be used as reactive groups for polymer attachment.

Preferably, in a conjugation reaction, from about 1.0 to about 10 moles of activated polymer per mole of polypeptide, depending on polypeptide concentration, is employed. Usually, the ratio chosen represents a balance between maximizing the reaction while minimizing side reactions (often non-specific) that can impair the desired pharmacological activity of the KIM-1 moiety. Preferably, at least 50% of the biological activity of the KIM-1 polypeptide is retained, and most preferably nearly 100% is retained.

The polymer can be conjugated to the KIM-1 polypeptide using conventional chemistry. For example, a polyalkylene glycol moiety can be coupled to a lysine epsilon amino group of the KIM-1 polypeptide. Linkage to the lysine side chain can be performed with an N-hydroxylsuccinimide (NHS) active ester such as PEG succinimidyl succinate (SS-PEG) and succinimidyl propionate (SPA-PEG). Suitable polyalkylene glycol moieties include, e.g., carboxymethyl-NHS, norleucine-NHS, SC-PEG, tresylate, aldehyde, epoxide, carbonylimidazole, and PNP carbonate. These reagents are commercially available. Additional amine reactive PEG linkers can be substituted for the succinimidyl moiety. These include, e.g., isothiocyanates, nitrophenylcarbonates, epoxides, and benzotriazole carbonates. Conditions preferably are chosen to maximize the selectivity and extent or reaction. Such optimization of reaction conditions is within ordinary skill in the art.

PEGylation can be carried out by any of the PEGylation reactions known in the art. See, e.g., *Focus on Growth Factors*, 3:4-10, 1992; published European patent applications EP 0 154 316 and EP 0 401 384. PEGylation may be carried out using an acylation reaction or an alkylation reaction with a reactive polyethylene glycol molecule (or an analogous reactive water-soluble polymer).

PEGylation by acylation generally involves reacting an active ester derivative of polyethylene glycol. Any reactive PEG molecule can be employed in the PEGylation. A preferred activated PEG ester is PEG esterified to N-hydroxysuccinimide (NHS). As used herein, "acylation" includes the following types of linkages between the therapeutic protein and a water soluble polymer such as PEG: amide, carbamate, urethane, and the like. See, e.g., *Bioconjugate Chem.* 5:133-140, 1994. Reaction parameters should be chosen to avoid temperature, solvent, and pH conditions that would damage or inactivate the KIM-1 polypeptide.

Preferably, the connecting linkage is an amide. Preferably, the at least 95% of the resulting product is mono-, di- or tri-PEGylated. However, some species with higher degrees of PEGylation may be formed in amounts depending on the specific reaction conditions used. Optionally, purified PEGylated species are separated from the mixture, particularly unreacted species, by conventional purification methods, including, e.g., dialysis, salting-out, ultrafiltration, ion-exchange chromatography, gel filtration chromatography, and electrophoresis.

PEGylation by alkylation generally involves reacting a terminal aldehyde derivative of PEG with KIM-1 in the presence of a reducing agent. In addition, one can manipulate the reaction conditions to favor PEGylation substantially only at the α-amino group of the N-terminus of KIM-1 (i.e., a mono-PEGylated protein). In either case of mono-PEGylation or poly-PEGylation, the PEG groups are preferably attached to the protein via a —$CH_2$—NH— group. With particular reference to the —$CH_2$— group, this type of linkage is known as an "alkyl" linkage.

Derivatization via reductive alkylation to produce a mono-PEGylated product exploits differential reactivity of different types of primary amino groups (lysine versus the N-terminal) available for derivatization. The reaction is performed at a pH that allows one to take advantage of the pKa differences between the ε-amino groups of the lysine residues and that of the α-amino group of the N-terminal residue of the protein. By such selective derivatization, attachment of a water soluble polymer that contains a reactive group such as an aldehyde, to a protein is controlled: the conjugation with the polymer takes place predominantly at the N-terminus of the protein and no significant modification of other reactive groups, such as the lysine side chain amino groups, occurs.

The polymer molecules used in both the acylation and alkylation approaches may be selected from among water soluble polymers as described above. The polymer selected should be modified to have a single reactive group, such as an active ester for acylation or an aldehyde for alkylation, preferably, so that the degree of polymerization may be controlled as provided for in the present methods. An exemplary reactive PEG aldehyde is polyethylene glycol propionaldehyde, which is water stable, or mono $C_1$-$C_{10}$ alkoxy or aryloxy derivatives thereof (see, U.S. Pat. No. 5,252,714). The polymer may be branched or unbranched. For the acylation reactions, the polymer(s) selected should have a single reactive ester group. For reductive alkylation, the polymer(s) selected should have a single reactive aldehyde group. Generally, the water soluble polymer will not be selected from naturally-occurring glycosyl residues since these are usually made more conveniently by mammalian recombinant expression systems.

Methods for preparing a PEGylated KIM-1 generally includes the steps of (a) reacting a KIM-1 protein or polypeptide with polyethylene glycol (such as a reactive ester or aldehyde derivative of PEG) under conditions whereby the molecule becomes attached to one or more PEG groups, and (b) obtaining the reaction product(s). In general, the optimal reaction conditions for the acylation reactions will be determined case by case based on known parameters and the desired result. For example, the larger the ratio of PEG:protein, the greater the percentage of poly-PEGylated product.

Reductive alkylation to produce a substantially homogeneous population of mono-polymer/KIM-1 generally includes the steps of: (a) reacting a KIM-1 polypeptide with a reactive PEG molecule under reductive alkylation conditions, at a pH suitable to pen-nit selective modification of the α-amino group at the amino terminus of KIM-1; and (b) obtaining the reaction product(s).

For a substantially homogeneous population of mono-polymer/KIM-1 polypeptide, the reductive alkylation reaction conditions are those that permit the selective attachment of the water soluble polymer moiety to the N-terminus of KIM-1. Such reaction conditions generally provide for pKa differences between the lysine amino groups and the α-amino group at the N-terminus (the pKa being the pH at which 50% of the amino groups are protonated and 50% are not). The pH also affects the ratio of polymer to protein to be used. In general, if the pH is lower, a larger excess of polymer to protein will be desired (i.e., the less reactive the N-terminal α-amino group, the more polymer needed to achieve optimal conditions). If the pH is higher, the polymer:protein ratio need not be as large. (Because more reactive groups are available, fewer polymer molecules are needed). For purposes of the present invention, the preferred pH is in the range of 3-9, preferably 3-6.

KIM-1 polypeptides can include a tag, e.g., a moiety that can be subsequently released by proteolysis. Thus, the lysine moiety can be selectively modified by first reacting a His-tag modified with a low molecular weight linker such as Traut's reagent (Pierce) which will react with both the lysine and N-terminus, and then releasing the his tag. The polypeptide will then contain a free SH group that can be selectively modified with a PEG containing a thiol reactive head group such as a maleimide group, a vinylsulfone group, a haloacetate group, or a free or protected SH.

Traut's reagent can be replaced with any linker that will set up a specific site for PEG attachment. By way of example, Traut's reagent could be replaced with SPDP, SMPT, SATA, or SATP (all available from Pierce). Similarly one could react the protein with an amine reactive linker that inserts a maleimide (for example SMCC, AMAS, BMPS, MBS, EMCS, SMPB, SMPH, KMUS, or GMBS), a haloacetate group (SBAP, SIA, SIAB), or a vinylsulfone group and react the resulting product with a PEG that contains a free SH. The only limitation to the size of the linker that is employed is that it cannot block the subsequent removal of the N-terminal tag.

In some embodiments, the polyalkylene glycol moiety is coupled to a cysteine group of the KIM-1 polypeptide. Coupling can be effected using, e.g., a maleimide group, a vinylsulfone group, a haloacetate group, and a thiol group.

Optionally, the KIM-1 polypeptide is conjugated to the polyethylene glycol moiety through a labile bond. The labile bond can be cleaved in, e.g., biochemical hydrolysis, proteolysis, or sulfhydryl cleavage. For example, the bond can be cleaved under in vivo (physiological) conditions.

The reactions may take place by any suitable method used for reacting biologically active materials with inert polymers, preferably at about pH 5-8, e.g., pH 5, 6, 7, or 8, if the reactive groups are on the alpha amino group at the N-terminus. Generally the process involves preparing an activated polymer and thereafter reacting the protein with the activated polymer to produce the soluble protein suitable for formulation.

One or more sites on a KIM-1 polypeptide can be coupled to a polymer. For example, one two, three, four, or five PEG moieties can be attached to the polypeptide. In some embodiments, a PEG moiety is attached at the amino terminus.

Anti-KIM-1 Antibodies

An anti-KIM-1 antibody or antigen-binding fragment thereof used according to the invention can be any of various types of molecules, including, but not limited to, a polyclonal antibody, monoclonal antibody (mAb), humanized antibody, fully human antibody, chimeric antibody, single-chain antibody, diabody, Fab fragment, Pab' fragment, F(ab')$_2$, Fv fragment, Fd fragment, dAb fragment, and complementarity determining region (CDR)-containing fragment.

As used herein: Pd means a fragment that consists of the $V_H$ and $C_{H1}$ domains; Fv means a fragment that consists of the $V_L$ and $V_H$ domains of a single arm of an antibody; and dAb means a fragment that consists of a $V_H$ domain (Ward et al., 1989, Nature 341:544-546). As used herein, single-chain antibody (scFv) means an antibody in which a $V_L$ region and a $V_H$ region are paired to form a monovalent molecules via a synthetic linker that enables them to be made as a single protein chain (Bird et al., 1988, Science 242:423-426; Huston et al., 1988, Proc. Natl. Acad. Sci. USA 85:5879-5883). As used herein, diabody means a bispecific antibody in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see e.g., Holliger, et al., 1993, Proc. Natl. Acad. Sci. USA 90:6444-6448; and Poljak et al., 1994, Structure 2:1121-1123.

Generally applicable methods for obtaining antibodies are known in the art. For a review of methods and materials useful for making anti-KIM-1 antibodies, see e.g., Harlow et al., 1988, Antibodies, A Laboratory Manual; Yelton, et al., 1981, Ann. Rev. Biochem., 50:657-80.; and Ausubel et al., 1989, Current Protocols in Molecular Biology (New York: John Wiley & Sons). Antigen-binding properties of anti-KIM-1 antibodies can be determined by one of ordinary skill in the art, using any of various conventional methods, including, e.g., radioimmunoassay, immunoblot assay and ELISA. Other suitable techniques for producing an antibody of the invention involve in vitro exposure of lymphocytes to a KIM-1 polypeptide, or screening of libraries of antibodies in phage or similar vectors. See, e.g., Huse et al., 1989. Science, 246:1275-1281.

Vectors

The invention provides vectors comprising the nucleic acids encoding KIM-1 polypeptides. The choice of vector and expression control sequences to which the nucleic acids of this invention is operably linked depends on the functional properties desired, e.g., protein expression, and the host cell to be transformed. A vector of the present invention may be at least capable of directing the replication or insertion into the host chromosome, and preferably also expression, of the structural gene included in the rDNA molecule.

Expression control elements useful for regulating the expression of an operably linked coding sequence are known in the art. Examples include, but are not limited to, inducible promoters, constitutive promoters, secretion signals, and other regulatory elements. When an inducible promoter is used, it can be controlled, e.g., by a change in nutrient status, or a change in temperature, in the host cell medium.

The vector can include a prokaryotic replicon, i.e., a DNA sequence having the ability to direct autonomous replication and maintenance of the recombinant DNA molecule extrachromosomally in a prokaryotic host cell, such as a bacterial host cell, transformed therewith. Such replicons are well known in the art. In addition, vectors that include a prokaryotic replicon may also include a gene whose expression confers a detectable marker such as a drug resistance. Typical of bacterial drug resistance genes are those that confer resistance to ampicillin or tetracycline.

Vectors that include a prokaryotic replicon can further include a prokaryotic or bacteriophage promoter for directing expression of the coding gene sequences in a bacterial host cell. Promoter sequences compatible with bacterial hosts are typically provided in plasmid vectors containing convenient restriction sites for insertion of a DNA segment of the present invention. Examples of such vector plasmids are pUC8, pUC9, pBR322 and pBR329 (BioRad Laboratories), pPL and pKK223 (Pharmacia). Any suitable prokaryotic host can be used to express a recombinant DNA molecule encoding a protein of the invention.

Eukaryotic cell expression vectors are known in the art and are commercially available. Typically, such vectors contain convenient restriction sites for insertion of the desired DNA segment. Exemplary vectors include pSVL and pKSV-10 (Pharmacia), pBPV-1, pML2d (International Biotechnologies), pTDT1 (ATCC 31255).

Eukaryotic cell expression vectors may include a selectable marker, e.g., a drug resistance gene. A preferred drug resistance gene confers neomycin resistance, i.e., the neomycin phosphotransferase (neo) gene (Southern et al., 1982, J. Mol. Anal. Genet. 1:327-341).

To express the antibodies or antibody fragments, DNAs encoding partial or full-length light and heavy chains are inserted into expression vectors. Expression vectors include plasmids, retroviruses, cosmids, YACs, EBV derived episomes, and the like. The expression vector and expression control sequences are chosen to be compatible with the expression host cell used. The antibody light chain gene and the antibody heavy chain gene can be inserted into separate vectors. In some embodiments, both genes are inserted into the same expression vector.

A convenient vector is one that encodes a functionally complete human $C_H$ or $C_L$ immunoglobulin sequence. Preferably, restriction sites engineered so that any $V_H$ or $V_L$ sequence can be easily inserted and expressed, as described above. In such vectors, splicing usually occurs between the splice donor site in the inserted J region and the splice acceptor site preceding the human C region, and also at the splice regions that occur within the human $C_H$ exons. Polyadenylation and transcription termination occur at native chromosomal sites downstream of the coding regions. The recombinant expression vector can also encode a signal peptide that facilitates secretion of the antibody chain from a host cell.

Preferred regulatory sequences for mammalian host cell expression include viral elements that direct high levels of protein expression in mammalian cells, such as promoters and enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al.

The recombinant expression vectors may carry sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr host cells with methotrexate selection/amplification) and the neo gene (for G418 selection).

Nucleic acid molecules encoding KIM-1 polypeptides and anti-KIM-1 antibodies, and vectors comprising these nucleic acid molecules, can be used for transformation of a suitable host cell. Methods for introduction of exogenous DNA into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors.

Transformation of host cells can be accomplished by conventional methods suited to the vector and host cell employed. With regard to transformation of prokaryotic host cells, electroporation and salt treatment methods can be employed (Cohen et al., 1972, *Proc. Natl. Acad. Sci. USA* 69:2110-2114). With regard to transformation of vertebrate cells, electroporation, cationic lipid or salt treatment methods can be employed. See, e.g., Graham et al., 1973, *Virology* 52:456-467; Wigler et al., 1979, *Proc. Natl. Acad. Sci. USA* 76:1373-1376).

Host cells can be prokaryotic or eukaryotic. Preferred eukaryotic host cells include, but are not limited to, yeast and mammalian cells. Examples of useful eukaryotic host cells include Chinese hamster ovary (CHO) cells (ATCC Accession No. CCL61), NIH Swiss mouse embryo cells NIH-3T3 (ATCC Accession No. CRL1658), and baby hamster kidney cells (BHK). Mammalian cell lines available as hosts for expression are known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, and a number of other cell lines.

Expression of polypeptides from production cell lines can be enhanced using known techniques. For example, the glutamine synthetase (GS) system is commonly used for enhancing expression under certain conditions. See, e.g., European Patent Nos. 0216846, 0256055, and 0323997 and European Patent Application No. 89303964.4.

Formulations

Compositions containing KIM-1 polypeptides, anti-KIM-1 antibodies, or antigen binding fragments of anti-KIM-1 antibodies may contain suitable pharmaceutically acceptable carriers. For example, they may contain excipients and/or auxiliaries that facilitate processing of the active compounds into preparations designed for delivery to the site of action. Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances that increase the viscosity of the suspension include, for example, sodium carboxymethyl cellulose, sorbitol and dextran. Optionally, the suspension may also contain stabilizers. Liposomes also can be used to encapsulate the molecules of the invention for delivery into cells or interstitial spaces. Exemplary pharmaceutically acceptable carriers are physiologically compatible solvents, dispersion media, coatings, antibacterial and antifungal agents, isotonic and absorption delaying agents, water, saline, phosphate buffered saline, dextrose, glycerol, ethanol and the like. In some embodiments, the composition comprises isotonic agents, for example, sugars, polyalcohols such as mannitol, sorbitol, or sodium chloride. In some embodiments, the compositions comprise pharmaceutically acceptable substances such as wetting or minor amounts of auxiliary substances such as wetting or emulsifying agents, preservatives or buffers, which enhance the shelf life or effectiveness of the active ingredients.

Compositions of the invention may be in a variety of forms, including, for example, liquid, semi-solid and solid dosage forms, such as liquid solutions (e.g., injectable and infusible solutions), dispersions or suspensions. The preferred form depends on the intended mode of administration and therapeutic application. In some embodiments, compositions are in the form of injectable or infusible solutions, such as compositions similar to those used for passive immunization of humans.

The composition can be formulated as a solution, micro emulsion, dispersion, liposome, or other ordered structure suitable to high drug concentration. Sterile injectable solutions can be prepared by incorporating the active ingredient in the required amount in an appropriate solvent with one or a combination of ingredients enumerated above, as required, followed by filtered sterilization. Generally, dispersions are prepared by incorporating the active ingredient into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof, the proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In some embodiments, the active ingredient is formulated with a controlled-release formulation or device. Examples of such formulations and devices include implants, transdermal patches, and microencapsulated delivery systems. Biodegradable, biocompatible polymers can be used, for example, ethylene vinyl acetate, polyanhydrides, polyglycolic acid, collagen, polyorthoesters, and polylactic acid. Methods for the preparation of such formulations and devices are known in the art. See e.g., *Sustained and Controlled Release Drug Delivery Systems,* 1978, J. R. Robinson, ed., Marcel Dekker, Inc., New York.

Supplementary active compounds also can be incorporated into the compositions. In some embodiments, a KIM-1 polypeptide, anti-KIM-1 antibody or fragment thereof is coadministered with a second immunomodulatory agent, e.g., BAFF-R-Ig, LTβ-R-Ig, CTLA4-Ig, anti-CD40L, or an anti-CD20 monoclonal antibody.

Dosage regimens may be adjusted to provide the optimum desired response. For example, a single bolus may be administered, several divided doses may be administered over time or the dose may be proportionally reduced or increased as indicated by the exigencies of the therapeutic situation. It is advantageous to formulate parenteral compositions in dosage unit form for ease of administration and uniformity of dosage unit form as used herein refers to physically discrete units suited as unitary dosages for the mammalian subjects to be treated, each unit containing a predetermined quantity of active compound calculated to produce the desired therapeutic effect in association with the required pharmaceutical carrier.

In some embodiments, a therapeutically effective dose for a KIM-1 polypeptide is in the range of 0.1 to 100 mg/kg. In some embodiments the therapeutically effective dose is in the range of 0.5 to 50 mg/kg. In some embodiments, the therapeutically effective dose is in the range of 1.0 to 10 mg/kg, e.g., about 5 mg/kg. Determination of a therapeutically effective dose can also be assessed by performing in vitro experiments that measure the concentration of the modifying agent required to coat target cells (KIM-1 or KIM-1-Receptor-positive cells depending on the modifying agent) for suitable (therapeutic) time periods. FACS and ELISA receptor-ligand binding assays can be used to monitor the cell coating reaction. Based on the results of such in vitro binding assays, a range of suitable modifying agent concentrations can be selected.

Molecules of the invention can be formulated into pharmaceutical compositions by admixture with pharmaceutically acceptable nontoxic excipients or carriers. Such compositions can be prepared for use in parenteral administration, particularly in the form of liquid solutions or suspensions. The composition can be administered in unit dosage form and can be prepared by any suitable method. Such methods are known in the art. For example, see *Remington's Pharmaceutical Sciences* (Mack Pub. Co., Easton, Pa. 1980).

Liquid dosage forms include pharmaceutically acceptable solutions, emulsions, microemulsions, and suspensions. In addition to the active compound, the liquid dosage form may contain inert ingredients including water, ethyl alcohol, ethyl carbonate, ethyl acetate, benzyl alcohol, benzyl benzoate, propylene glycol, 1,3-butylene glycol, dimethylformamide, oils, glycerol, tetrahydrofurfuryl alcohol, polyethylene glycols, fatty acid esters of sorbitan, and mixtures thereof.

Injectable depot formulations can be made by forming microencapsulated matrices of the drug in biodegradable polymers such as polylactide-polyglycolide. Depending on the ratio of drug to polymer, and the nature of the polymer employed, the rate of drug release can be controlled. Other exemplary biodegradable polymers include polyorthoesters and polyanhydrides. Depot injectable formulations also can be prepared by entrapping the drug in liposomes or microemulsions that are compatible with body tissues.

EXAMPLES

The invention is further illustrated by the following experimental examples. The examples are provided for illustrative purposes only, and are not to be construed as limiting the scope or content of the invention in any way.

Example 1

Human KIM-1 Extracellular Domain-Fc Construct (pHI105)

The extracellular domain (residues 1-290) of human KIM-1 was fused to the Fc portion of human IgG1 (hinge, CH2, CH3) and cloned into pEAG347, a Biogen mammalian expression plasmid. The plasmid contained a tandem promotor for constitutive expression and the dihydrofolate reductase gene for methotrexate selection of stably expressing cell lines. The amino acid sequence of the encoded fusion polypeptide was as follows:

```
                                                              (SEQ ID NO:3)
1         10        20        30        40        50        60
MHPQVVILSLILHLADSVAGSVKVGGEAGPSVTLPCHYSGAVTSMCWNRGSCSLFTCQNG 70        80        90       100       110       120
IVWTNGTHVTYRKDTRYKLLGDLSRRDVSLTIENTAVSDSGVYCCRVEHRGWFNDMKITV 130       140       150       160       170       180
SLEIVPPKVTTTPIVTTVPTVTTVRTSTTVPTTTTVPTTTVPTTMSIPTTTTVPTTMTVS 190       200       210       220       230       240
TTTSVPTTTSIPTTTSVPVTTTVSTFVPPMPLPRQNHEPVATSPSSPQPAETHPTTLQGA 250       260       270       280       290       300
IRREPTSSPLYSYTTDGNDTVTESSDGLWNNNQTQLFLEHSLLTANTTKGVDKTHT CPPC 310       320       330       340       350       360
PAPELLGGPSVFLFPPKPKDTLMISRTPEVTCVVVDVSHEDPEVKFNWYVDGVEVHNAKT 370       380       390       400       410       420
KPREEQYNSTYRVVSVLTVLHQDWLNGKEYKCKVSNKALPAPIEKTISKAKGQPREPQVY 430       440       450       460       470       480
TLPPSRDELTKNQVSLTCLVKGFYPSDIAVEWESNGQPENNYKTTPPVLDSDGSFFLYSK 490       500       510       518
LTVDKSRWQQGNVFSCSVMHEALHNHYTQKSLSLSPGK
```

The signal sequence is indicated by an underline. The Fc hinge is indicated by a box.

Example 2

Human KIM1$_{ECDmucin\Delta}$-Fc (pHI100)

DNA encoding residues 1-129 of human KIM-1 fused to the Fc portion of human IgG1 (hinge, CH2, CH3) was cloned into pEAG347, a Biogen mammalian expression plasmid containing a tandem promotor for constitutive expression and the dihydrofolate reductase gene for methotrexate selection of stably expressing cell lines. The amino acid sequence of the encoded fusion polypeptide was as follows:

(SEQ ID NO:4)
```
         10        20        30        40        50        60
MHPQVVILSLILHLADSVAGSVKVGGEAGPSVTLPCHYSGAVTSMCWNRGSCSLFTCQNG 70        80        90       100       110       120
IVWTNGTHVTYRKDTRYKLLGDLSRRDVSLTIENTAVSDSGVYCCRVEHRGWFNDMKITV 130       140       150       160       170       180
SLEIVPPKVVDKTHTCPPCPAPELLGGPSVFLFPPKPKDTLMISRTPEVTCVVVDVSHED 190       200       210       220       230       240
PEVKFNWYVDGVEVHNAKTKPREEQYNSTYRVVSVLTVLHQDWLNGKEYKCKVSNKALPA 250       260       270       280       290       300
PIEKTISKAKGQPREPQVYTLPPSRDELTKNQVSLTCLVKGFYPSDIAVEWESNGQPENN 310       320       330       340       350
YKTTPPVLDSDGSFFLYSKLTVDKSRWQQGNVFSCSVMHEALHNHYTQKSLSLSPGK
```

Example 3

Human KIM1$_{ECD}$-6xHis (PVB602)

The extracellular domain (residues 1-290) of human KIM-1 was fused to a short C-terminal peptide [VEHHH-HHH; SEQ ID NO:5] including a repeat of 6 histidine residues and cloned into pCA125, a BIOGEN mammalian expression plasmid containing a CMV promotor for transient constitutive expression in mammalian cells. The amino acid sequence of the encoded fusion polypeptide was as follows:

(SEQ ID NO:7)
```
         10        20        30        40        50        60
MHPQVVILSLILHLADSVAGSVKVGGEAGPSVTLPCHYSGAVTSMCWNRGSCSLFTCQNG 70        80        90       100       110       120
IVWTNGTHVTYRKDTRYKLLGDLSRRDVSLTIENTAVSDSGVYCCRVEHRGWFNDMKITV 130       140       150       160       170       180
SLEIVPPKVTTTPIVTTVPTVTTVRTSTTVPTTTTVPTTTVPTTMSIPTTTTVPTTMTVS 190       200       210       220       230       240
TTTSVPTTTSIPTTTSVPVTTTVSTFVPPMPLPRQNHEPVATSPSSPQPAETHPTTLQGA 250       260       270       280       290
IRREPTSSPLYSYTTDGNDTVTESSDGLWNNNQTQLFLEHSLLTANTTKGVEHHHHHH
```

Example 4

Murine KIM-1-Fc Fusion

A PCR-amplified ectodomain of murine kim-1 flanked by NotI and SalI sites was fused with human IgG1Fc (isolated from EAG409 as a SalI-NotI fragment) and cloned into Ebna 293 cell expression vector CH269 (construct PEM073-6) and CHO cell expression vector pV90 (construct PEM078-1). The SalI site is at the junction between kim1 and Fc. The resulting nucleotide sequence of the ORF for the fusion protein was as follows (SalI site in upper case):

(SEQ ID NO:8)
```
atgaatcagattcaagtcttcatttcaggcctcatactgcttctcccagg cactgtggattcttatgtggaagtaaaggggggtagtgggtcaccctgtca cacttccatgtacttactcaacatatcgtggaatcacaacgacatgttgg ggccgagggcaatgcccatcttctgcttgtcaaaatacacttatttggac caatggacatcgtgtcacctatcagaagagcagtcggtacaacttaaagg
```

-continued
```
ggcatatttcagaaggagatgtgtccttgacgatagagaactctgttgag agtgacagtggtctgtattgttgtcgagtggagattcctggatggtttaa tgatcagaaagtgaccttttcattgcaagttaaaccagagattcccacac gtcctccaacaagacccacaactacaaggcccacagctacaggaagaccc acgactatttcaacaagatccacacatgtaccaacatcaatcagagtctc
```

-continued

```
tacctccactcctccaacatctacacacacatggactcacaaaccagaac ccactacattttgtccccatgagacaacagctgaggtgacaggaatccca tcccatactcctacagactggaatggcactgcgacatcctcaggagatac ctggagtaatcacactgaagcaatccctccagggaagccgcagaaaaccc tactaagggcGTCGACaaaactcacacatgcccaccgtgcccagcacctg aactcctgggggaccgtcagtcttcctcttccccccaaaacccaaggac accctcatgatctcccggacccctgaggtcacatgcgtggtggtggacgt gagccacgaagaccctgaggtcaagttcaactggtacgtggacggcgtgg aggtgcataatgccaagacaaagccgcgggaggagcagtacaacagcacg taccgtgtggtcagcgtcctcaccgtcctgcaccaggactggctgaatgg caaggagtacaagtgcaaggtctccaacaaagccctcccagcccccatcg agaaaaccatctccaaagccaaagggcagccccgagaaccacaggtgtac accctgcccccatcccgggatgagctgaccaagaaccaggtcagcctgac ctgcctggtcaaaggcttctatcccagcgacatcgccgtggagtgggaga gcaatgggcagccggagaacaactacaagaccacgcctcccgtgttggac tccgacggctccttcttcctctacagcaagctcaccgtggacaagagcag gtggcagcaggggaacgtcttctcatgctccgtgatgcatgaggctctgc acaaccactacacgcagaagagcctctccctgtctccgggaaatga
```

The translated sequence of mukim-1 ectodomain-human Fc was as follows. Two junction amino acids contributed by the SalI site are indicated in bold:

(SEQ ID NO:9)
MNQIQVFISGLILLLPGTVDSYVEVKGVVGHPVTLPCTYSTYRGITTTCW

GRGQCPSSACQNTLIWTNGHRVTYQKSSRYNLKGHISEGDVSLTIENSVE

SDSGLYCCRVEIPGWFNDQKVTFSLQVKPEIPTRPPTRPTTTRPTATGRP

TTISTRSTHVPTSIRVSTSTPPTSTHTWTHKPEPTTFCPHETTAEVTGIP

SHTPTDWNGTATSSGDTWSNHTEAIPPGKPQKNPTKGVDKTHTCPPCPAP

ELLGGPSVFLFPPKPKDTLMISRTPEVTCVVVDVSHEDPEVKFNWYVDGV

EVHNAKTKPREEQYNSTYRVVSVLTVLHQDWLNGKEYKCKVSNKALPAPI

EKTISKAKGQPREPQVYTLPPSRDELTKNQVSLTCLVKGFYPSDIAVEWE

SNGQPENNYKTTPPVLDSDGSFFLYSKLTVDKSRWQQGNVFSCSVMHEAL

HNHYTQKSLSLSPGK

Example 5

KIM-1-Fc Fusion in Murine SRBC Model

The immune response of rodents to sheep red blood cells (SRBC) depends upon competent T cell interaction with APCs and B cells. Therefore the anti-SRBC response is a useful model to examine the role that cellular proteins on lymphocytes and APC play in the development and maturation of the immune response. The anti-SRBC response in mice consists of production of IgM and of the various IgG isotypes, including high levels of the IgG1 isotype, with considerable levels of IgG2a and IgG2b seen as well. IgG1 is considered to be an isotype that is driven by a Th2-mediated immune response, which is characterized by the expression of cytokines such as Il-4-Il5, and Il-13. IgG2a and IgG2b isotypes are more characteristic of a Th1-driven immune response, and are associated with expression of Il-12. Finally, the IgG3 isotype is typical of T-independent immune responses. All 4 isotypes are represented in the anti-SRBC response.

The course of the anti-SRBC response was followed in mice treated with murine KIM-1-Ig fusion protein (mKIM-1-Ig) to interrupt KIM-1-dependent activity on T cells. Mice were treated the day before challenge (D-1) with 150 ugs/mouse mKIM-1-g, challenged with 100 µl of a 10% solution of SRBC (Colorado Serum Company) in PBS on day 0, then treated again with 150 µg of mKIM-1-Ig on days 3 and 6. The mice were bled for a serum samples on days 7, 14, 21, and 30 following immunization, and anti-SRBC antibody titers were obtained using the hemagglutination assay. This assay relied on the ability of antibodies to crosslink and cluster ("agglutinate") SRBC based on their pentameric structure (for IgM) or on the presence of a third species anti-idiotypic antisera (for the Ig classes).

In brief, the protocol was as follows. Serum samples were diluted as appropriate (1:15 to 1:200, depending on the isotype being measured, and the day of the response) then titered in 1:2 steps using 96 well assay plates which we obtained from Corning (Costar® #3795). For the IgM assay, the sera samples were assayed in duplicate. 25 µl of 10% SRBC in glucose-PBS (G-PBS) was added to the wells and the agglutination response was allowed to develop for 1 hour at 37° C. For the Ig assays, serum samples were loaded into the plates and diluted in triplicate. 25 µl of 1% 2-mercaptoethanol (Sigma), diluted in G-PBS, was added to each serum sample series, then the plate was incubated for 30 minutes at 37° C. This was done to break all the disulfide bonds which hold together IgM pentamers, and thus to elimiante any IgM background. Then, 25 µl of 10% SRBC in G-PBS, and 25 µl of a 1:250 dilution in G-PBS of anti-idiotypic antisera (goat anti-mouse IgG1, IgG2a, IgG2b, or IgG3, all from Southern Biotechnology Associates) was added to the first 2 of each triplicate to cross-link the anti-SRBC IgGs of that subtype present. The third well of each triplicate was left uncrosslinked to serve as a control for any residual IgM activity that might have survived the 2-mercaptoethanol treatment. The plates were incubated for 1 hour at 37° C. All assay plates were left overnight at 4° C. to stabilize the resulting hemagglutination before being scored and photographed. All titers were scored as the last dilution that gave a positive agglutination readout.

Figure 4:
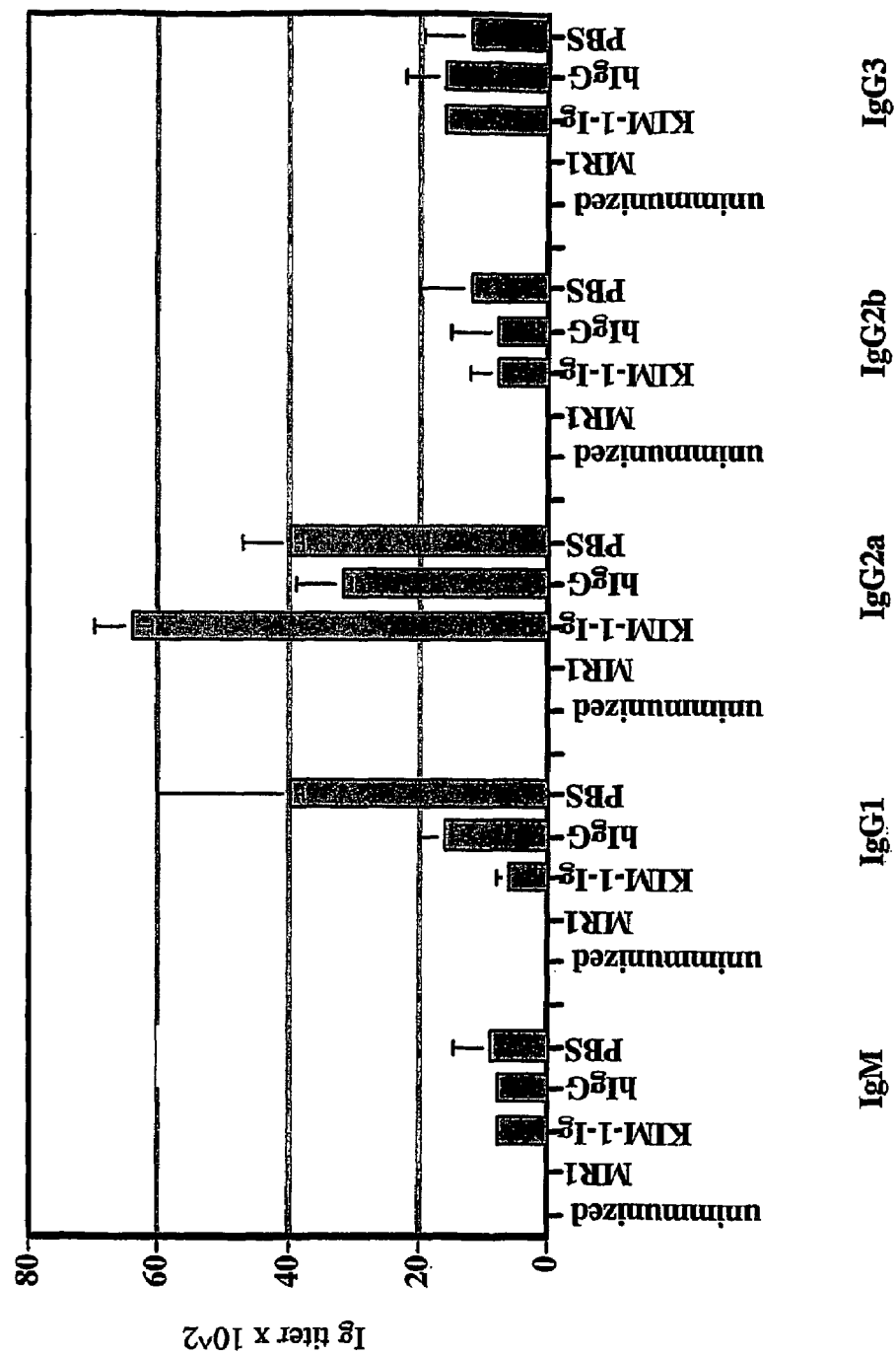
FIG. 4 is a histogram summarizing immunoglobulin titers measured on day 14 in Balb/c mice receiving a primary challenge with sheep red blood cells (experiment 2).
Figure 5:
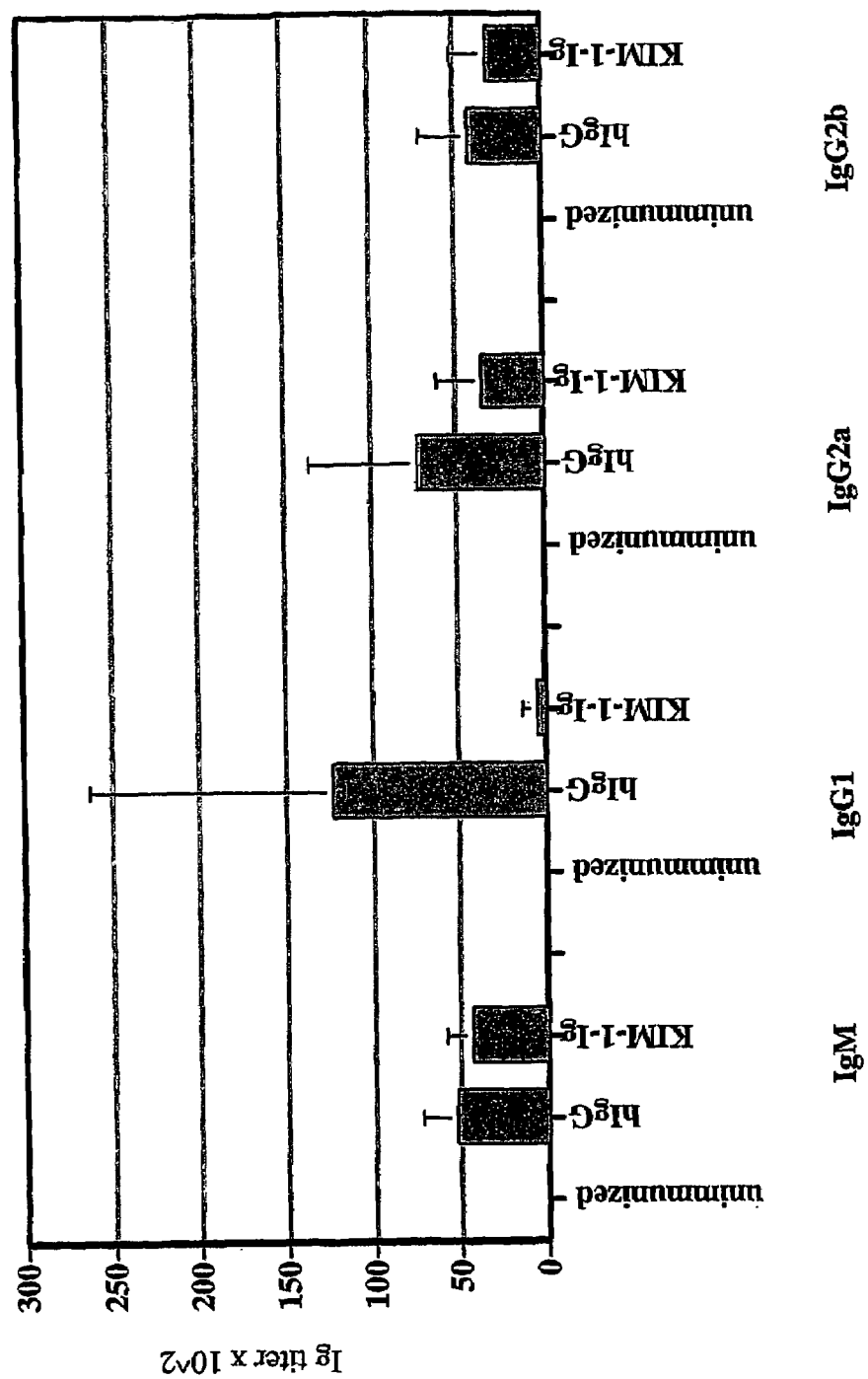
FIG. 5 is a histogram summarizing immunoglobulin titers measured on day 7 in C57B1/6 mice receiving a primary challenge with sheep red blood cells.
Figure 6:
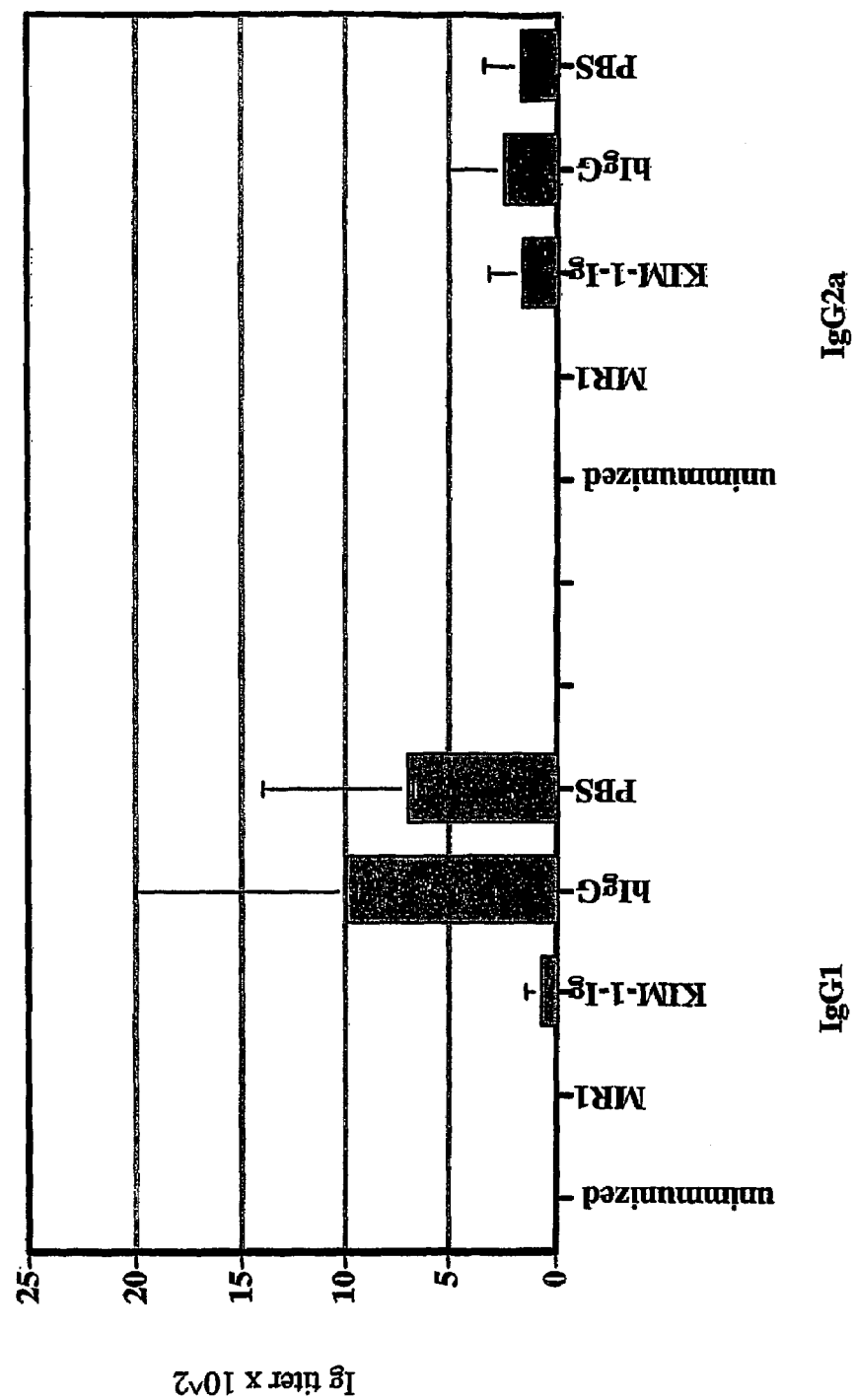
FIG. 6 is a histogram summarizing immunoglobulin titers measured in mice from experiment 1 after being allowed full recovery from the primary challenge (FIG. 3) and then rechallenged. Immunoglobulin titer was measured on day 3 after rechallenge.
Figure 7:
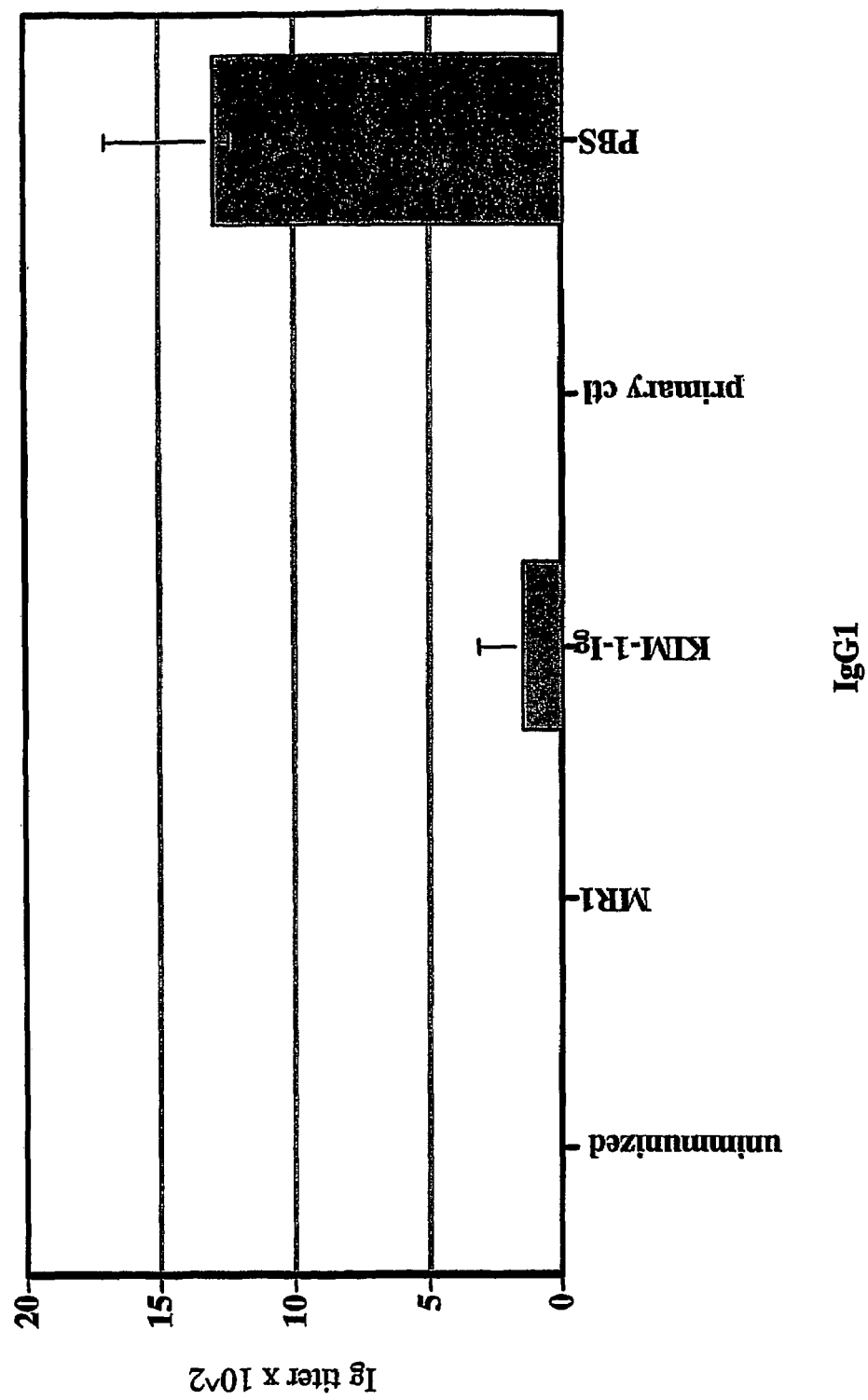
FIG. 7 is a histogram summarizing immunoglobulin titers measured in mice from experiment 2 after being allowed full recovery from the primary challenge (FIG. 4) and then rechallenged. Immunoglobulin titer was measured on day 3 after rechallenge.

The effect of mKIM-1-Ig treatment on the anti-SRBC response was compared to control groups of mice not challenged with SRBC, or challenged with SRBC but dosed with anti-CD40L, nonspecific polyclonal hIgG, or PBS. The unchallenged and anti-CD40L-treated mice had no anti-SRBC response, as expected. The mice given SRBC and dosed either with PBS or hIgG had robust antibody titers to all classess of Ig tested. The mice treated with mKIM-1-Ig in contrast had a very striking and specific defect in the IgG1 anti-SRBC isotype. In 2 independent experiments using the Balb/c strain of mice, markedly defective levels of IgG1 anti-SBRC were detected (FIGS. 3 and 4). Seven days after induction of the anti-SRBC response the IgG1 titer was on avaerage 70% lower in mKIM-1-Ig treated mice than in control treated mice. By day 14 after induction of the anti-SRBC response the IgG1 titer was reduced by more than 85%. A similar defect was observed in 1 experiment using the C57Bl/6 strain of mice (FIG. 5). Balb/c mice and C57Bl/6 mice are considered to have different biases in their immune responses, with Balb/c mice being characterized as having a predominantly Th2-mediated response and C57B1/6 mice having a predominantly Th1-mediated response. Therefore, in these mouse strains the ability of murine KIM-1-Ig fusion protein to block the IgG1 isotype production overrode inherent Th-biases in the strains. Surprisingly, the effect of mKIM-1-Ig treatment extended to the secondary response, whereby no IgG1 was produced by memory B cells in response to subsequent SRBC challenge (FIGS. 6 and 7).

Example 6

Graft Versus Host Disease (GVHD)

GVHD is modeled in the mouse using parental into F1 cell transplantation regimens. Splenocytes from the DBA2 strain of mice are injected iv into (DBA2×C57B1/6) F1 mice, which are referred to as B6D2F1. The injected splenocytes constitute the graft, and the DBA2 mouse is the donor of that graft. The F1 mouse which receives the graft is the host. Donor T cells present in the graft recognize half of the MHC markers (haplotypes) on host cells as foreign, because they are derived from the other, C57B1/6 parent. This induces a donor T cell response against the host resulting in GVHD. When DBA/2 parental splenocytes are injected into the B6D2F1 host, chronic GVHD develops. In contrast, when C57B1/6 splenocytes are injected into the B6D2F1 host, acute GVHD develops. Although it remains unclear what underlying mechanism is responsible for the distinct disease outcomes using these 2 injection protocols it is believed that the cytokines expressed by the cells contained within the DBA/2 splenocyte graft favor the development of chronic GVHD while the cytokines expressed by the cells contained within the C57B1/6 splenocyte graft favor the development of acute GVHD. Reagents which interfere with T cell interactions with antigen presenting cells (e.g., dendritic cells, macrophages, B cells: APC) effectively block both acute and chronic GVHD.

KIM-1 antagonists modify the development of an immunological response in a mouse model of chronic GVHD. The ability to block chronic GVHD includes effects on B cell activation and proliferation, and on the generation of secreted IgG. Mice are treated intraperitoneally (ip) with KIM-1 antagonists or modifying agents, control treatments, or are left untreated. 4 hours later mice receive $1 \times 10^8$ splenocytes isolated from DBA/2 mice, in an 0.5 ml injection given intraveneously (iv). The iv injected DBA/2 splenocytes constituted the allograft. 2, 4, and 6 days after the graft is given, the mice are again treated with KIM-1 antagonists or modifying agents or with control treatments. An additional control group of mice receives $1 \times 10^8$ B6D2F1 splenocytes, which cannot induce disease in B6D2F1 recipients. Alternatively, ungrafted and untreated B6D2F1 mice are used as controls. Fourteen days after the graft is given the mice are sacrificed and examined for evidence of disease.

Untreated graft-recipient mice manifest a variety of symptoms that are indicative of the development of chronic GVHD. Splenomegaly, or enlargement of the spleen, is evidence that donor T cells and host B cells have become activated, and are undergoing polyclonal expansion, with dramatic increases in cell number. The appearance of cell surface proteins such as CD69 on a subset of B cells is indicative of B cell activation. The loss of L-selectin molecules from CD4+ and CD8+ T cells is evidence of T cell activation. The secretion of Ig molecules, such as IgG classes, IgA, and IgE, either into the serum, or in in vitro cell culture assays, indicates that B cells have become activated, and have switched their Ig class. In this regard the appearance of anti-self Igs in the serum or in in vitro cell culture assays shows that Igs that are being produced have inappropriate autoantigen recognition. Finally, survivorship can be measured as an outcome of different treatment regimens. Treatment with KIM-1 antagonists (e.g., KIM-1-Ig) or blocks these readouts of the development of chronic GVHD, as shown by reduction in the extent of splenomegaly, reduction in the polyclonal expansion of lymphocyte populations, reduction in the appearance or disappearance of cell surface markers indicating lymphocyte activation, reduction of Ig secretion, and/or reduction in mortality.

We compare control mice to untreated allograft-recipient mice to examine the extent of splenomegaly, B cell activation, and Ig secretion during GVHD. Anti-CD40L mAb MR1 is used as a positive control in these experiments, since it has been previously shown that blocking the CD40L/CD40 interaction is an effective means of interfering with the development of chronic GVHD (urie et al., 1994, *J. Clin. Invest.* 94: 1333-1338). To investigate cell populations affected by treatment with KIM-1 antagonists FACS analyses are performed on splenocytes taken from the recipient mice 14 days after graft injection. Spleen cells from 34 mice per group are isolated and pooled. Activation of recipient B cells is a defining feature of chronic GVHD. In mice undegoing chronic GVHD a small but readily visible proportion of the B200+B cells express the activation marker CD69. Therefore CD69 expression is used as a measure of the extent of disease. Total IgG in cultures of splenocytes in mice from different treatment groups is also determined, sice the expression of CD69 by B cells is indicative of their activation state.

In the mouse model the development of the disease is dependent on the Th2 cytokine Il4, and can be blocked by treating with anti-Il4 mAb. Such treatment blocks the expansion of host B cells, and the concomitant hyper-Ig production. The development of GVHD can be followed in a number of ways. The expansion of the donor T cell and host B cell populations is measured by the spleen index, which is the ratio of spleen weight to body weight, normalized to control (non-diseased) mice. The activation of B cells in diseased mice is measured using analyses of B cell activation markers. Finally, the effects of B cell activation is seen in the levels of Ig in circulation (e.g., in serum) or produced by cultures of host splenocytes harvested several weeks after disease induction. Circulating Ig in diseased animals will contain anti-self antibodies. Ultimately, diseased animals succumb to kidney and other organ failure due to accumulated Ig deposition, and therefore survivorship is a relevant measure of disease activity.

Example 7

SCID-hu Mouse Models

It is possible to study human immune responses in the SCID-hu mouse. For example, SCID mice are injected intraperitoenally with $2\text{-}5 \times 10^7$ human peripheral blood mononuclear cells, and these cells reside and function in the gut for some time, and respond to antigen challenge. NOD-SCID mice are reconstituted with human PBLs and these mice have the additional advantage of the seeding of human cells (T, B, APC) into the spleen, where systemic immune responses may be supported. Appropriate models are discussed in Berney et al., 2001, *Transplantation* 72:133-140. Other models of immune responses use the SCID/beige mouse and involve cotransplantation of PBLs or fetal cells with fetal mesenteric lymph nodes to provide support for immune responses (Carballido et al., 2000, *Nat. Med.* 6:103-106.

SCID-hu or NOD-SCID-hu mice are reconstituted with peripheral blood mononuclear cells (PBMCs) isolated from tetanus-toxoid (TT) immunized human donors. SCID-hu mice so reconstituted have human cells residing in various compartments, including the peritoneum. NOD-SCID-hu mice so reconstituted have human T cells residing in various compartments including within their secondary lymphoid organs, such as the spleen. Primary immune responses are induced in these reconstituted mice by immunization with antigen coupled to TT, or to an antigenic portion of TT, or to liposomes, or to liposomes containing TT. Mice so reconstituted and challenged produce a high titer (>1:1000) Ig response to antigen (e.g., NP, DNP, KLH, OVA, HIV gp120 or portions thereof, melanoma-associated antigen GD2, and ovine mucin, are just a few of many examples). Some examples are presented in Ifverson et al., 1995, *Immunology* 84:111-116. Mice so reconstituted and then treated with KIM-1 antagonists or modifying agents do not produce a high titer to antigen challenge.

In another methodology, SCID-hu mice are reconstituted with fetal human bone, thymus, fragments of skin, and mesenteric lymph nodes (MLN). The presence of MLN is sufficient to support robust immune responses to TT-immunization (and, since all donor tissue is fetal, this is strictly a primary immune response). This model is discussed in detail in Carballido et al., 2000, *Nat. Med.* 6:103-106. TT-immunization causes human lymphocyte proliferation, and activation, and IgM and IgG-secretion by B cells. Treatment of SCID mice so reconstituted with KIM-1 antagonists or modifying agents reduces the human lymphocyte proliferation, activation, and the secretion of immunoglobulins upon TT-challenge.

In a modification of these models, or other similar NOD-SCID-hu or SCID-hu models, secondary immune responses are measured in a disease setting, e.g., of delayed type hypersensitivity (DTH). In this instance the TT-challenge is given in the footpad of SCID or NOD-SCID mice reconstituted with PBMCs from TT-immune individuals, and the swelling of the footpad is measured in response. The DTH responses relies on the presence of human memory T cells in circulation in the reconstituted mouse. Such models can also be used to detect the possible rejection of donor tissue in transplant patients, as in the "trans vivo" models. An example of this type of approach is discussed in Carrodeguas et al., 1999, *Hum. Immunol.* 60: 640-651. Treatment of mice so reconstituted with KIM-1 antagonists or modifying agents prevents DTH responses. Other models of human disease responses in the SCID mouse include transfer of splenocytes or PBMCs from autoimmune patients in the mouse, whereby they continue expression of immunoglobulins and other markers of disease (see Martino and Grinaldim 1997, In: *Immunology Methods Manual*, vol 3. Lefkovits, ed. Academic Press, San Diego). Treatment of these mice with KIM-1 antagonists or modifying agents prior to the transfer of autoimmune cells from patients reduces the expression of immunoglobulins or other markers of the autoimmune pathology.

A very valuable methodology utilizing the SCID mouse involve the xenografting of disease tissue onto the recipient mouse. Methods of transferring skin from psoriasis or atopic dermatitis patients for instance are widely used models of these diseases. Atopic dermatitis is a Th2 mediated cellular immune disease that can be modeled in SCID mice by transferring the PBMCs and biopses of skin together to the recipient mouse. Treatment of these mice with KIM-1 antagonists or modifiers prevents the cellular accumulation and local cytokine secretion which is evidence of activation of lymphocytes and effector cells (eosinophils, basophils, etc.) in the skin graft. This is evidence of efficacy in preventing dermatitis in the donor patient.

Example 8

Other Murine Models of Atopic Disease

Useful models of allegy, asthma, airway hypersensitivity (AHR), and other atopic diseases are run in the mouse. For example, allergic skin inflammation is induced by epicutaneous sensitization with antigen. In one example the antigen is ovalbumin (OVA). The Th2 response to this sensitization is shown by the presence of eosinophils in the skin, local expression in the skin of Th2 cytokines, and airway hyperresponsiveness (AHR) to inhaled antigen. Eosinophils are absent from the skin of OVA-sensitized mice that are first treated with KIM-1 antagonists or modifiers, and the level of Th2 cytokines is reduced. Mice that are repeatedly sensitized produce OVA-specific IgE, and their splenocytes secrete the Th2 cytokines IL-4 and IL-5 following in vitro stimulation with OVA. These readouts of the Th2 immune response are blocked upon treatment with KIM-1 antagonists or modifiers. Alternatively, mice (e.g., BALB/c mice) can be sensitized with an i.p. injection of antigen (day 0), then rechallenged with intranasal antigen 3 weeks later (once) and 4 weeks later (3 times: days 26, 27, 28, e.g.). This produces lung hyperresponsiveness (AHR), which is mediated by Th2 cytokines such as IL-13. This Th2 immune response is blocked upon treatment with KIM-1 antagonists or modifiers Using the OVA-specific TCR transgenic model (DO11.10), we induce an OVA-specific immune response, then transfer Th2 OVA-specific T cells to naive recepients, which then are challenged with OVA-aerosal. These mice rapidly develop antigen-specific AHR. This response is blocked when mice are treated with KIM-1 antagonists or modifiers prior to OVA aerosal challenge.

Methacholine aerosol treatment induces the recruitment of eosinophils to the lung, causing AHR in mice. Treatment of mice with KIM-1 antagonists or modifying agents will block AHR development.

Example 9

Collagen-Induced Arthritis

In this murine model of arthritis, collagen is used to trigger T cell-mediated B cell activation and autoantibody production, which attacks the joints, resulting in a condition which resembles rheumatoid arthritis. In various stains of mice this response is dominated by high titers of IgG1. In particular, in mice lacking Il-12 by genetic deficiency (Il-12 knockout mice: Il-12-/-) the IgG1 titer is very high, and these Abs effectively mediate joint destruction.

Mice are treated with collagen in complete freund's adjuvant by injecting intradermally at 2 sites: a small volume delivered to each ear, and a small volume delivered to the skin between the shoulders. Three weeks later the mice are boosted with soluble collagen in saline, using an intraperitoneal route. Within a week, joint damage is assessed by measuring the swelling of the joint with a caliper and by measuring antibody titers. Treatment of mice during the course of disease development ameliorates disease score. In particular, treatment with 0.1-1 mg/kg of KIM-1 antagonists or modifying agents the day prior to disease initiation, followed by treatments thereafter, will block disease development, as assessed by reduced joint swelling and reduced immunolglobulin titers. This is a prophylatic course of treatment.

Treatment with KIM-1 a antagonist after induction, and prior to boosting, ameliorates disease development, as assessed by reduced joint swelling and reduced immunolglobulin titers. This is a therapeutic course of treatment. Treatment with KIM-1 antagonists or modifying agents after the boost injection blocks disease development, as assessed by reduced joint swelling and reduced immunolglobulin titers. This is a therapeutic course of treatment.

Example 10

Murine Models of LuPus

In the NZB/W model, mice from the NZB strain are mated with mice from the NZW strain, and the F1 progeny develop a lupus like disease over time. Manifestations of disease include the production of auto-antibodies and rheumatoid factor. Ig-deposition in the kidney results from the high amount of Ig and RF produced, leading to decreased kidney function over time, as can be measured by proteinuria in the urine.

The NZB/W F1 progeny begin to manifest symptoms of disease at around 5 months of age, with moderate proteinuria scores at that time (PU of 2). By 9 months of age the mice will have reached a maximum PU=4, and will begin to succomb to disease as a consequence of kidney failure. Another model called SNF1 (SWR×NZB F1 cross) follows similar kinetics.

Mice are treated with 0.1-1 mg/kg of KIM-1 antagonists the day prior to disease initiation, followed by treatments thereafter. This blocks disease development, as measured by the PU score, and/or by measuring titers of immunoglobulin in the serum, and/or by immunohistochemical analysis of hyperplasia in the spleen, and/or by immunohistochemical analysis of immune complex deposition and changes in the structure of the glomeruli in the kidney.

Treatment with KIM-1 antagonists after induction of disease, for example at the 5th month, but prior to severe disease (i.e., PU=2-3, ameliorates disease development or reverses disease damage. This can be measured by the PU score, and/or by measuring titers of immunoglobulin in the serum, and/or by immunohistochemical analysis of hyperplasia in the spleen, and/or by immunohistochemical analysis of immune complex deposition and changes in the structure of the glomeruli in the kidney.

Treatment with KIM-1 antagonists after disease is severe (PU=3-4) blocks disease development or reverses disease damage. This can be measured by the PU score, and/or by measuring titers of immunoglobulin in the serum, and/or by immunohistochemical analysis of hyperplasia in the spleen, and/or by immunohistochemical analysis of immune complex deposition and changes in the structure of the glomeruli in the kidney.

Example 11

Mixed Lymphocyte Reaction (MLR)

Mouse MLR assays and antagonism of KIM-1. Mixed lymphocyte reactions (MLR) were run as follows: Spleens were isolated from C57B16 and Balb/c mice using sterile technique, ground roughly to release lymphocytes, then treated with a hypotonic solution (Gey's solution) to lyse red blood cells. The remaining cells were seperated from residual tissue by passing them through a cell strainer (BD Falcon, Bedford, Mass. USA), and then were washed with sterile, pyrogen-free PBS, and centrifuged to pellet the cells. The cells were resuspended in the PBS solution a second time, pelleted again, then resuspended in complete RPMI media. The cells were counted and diluted as necessary. The Balb/c lymphocytes were used as the stimulator cells, therefore, these were irradiated at 3000 RAD prior to use.

To set up the assays, stimulator cells were added to the well as varying ratios relative to the number of responder cells ($2 \times 10^5$/well). Media was supplemented with rat anti-KIM-1 antibodies, or KIM-1-Ig fusion protein and control-Ig fusion proteins at 20 µg/ml, as indicated. Cultures were set up in three identical plates, and each experimental condition was represented by 3 wells per plate. One plate was used to generate cell proliferation data using an MTS assay (CellTiter 96, Promega, Madison, Wis. USA). The other plates were used to collect supernatant samples for cytokine analyses. ELISAs (Pierce Endogen, Rockford, Ill. USA) were used to measure the levels of mIFNγ, mTNF, and mIl-2 in culture supernatants. Standard errors for values derived from the proliferation assays and ELISAs were less than 10%, and have been omitted from the figures. Large deviations from the positive control values for IFNγ were noted, while the levels of Il-2 and TNF in the cultures were not significantly different between the positive control and treatment groups. Therefore, the Il-2 and TNF data have been omitted; the data for IFNγ and cell proliferation are shown for each representative experiment.

Figure 8:
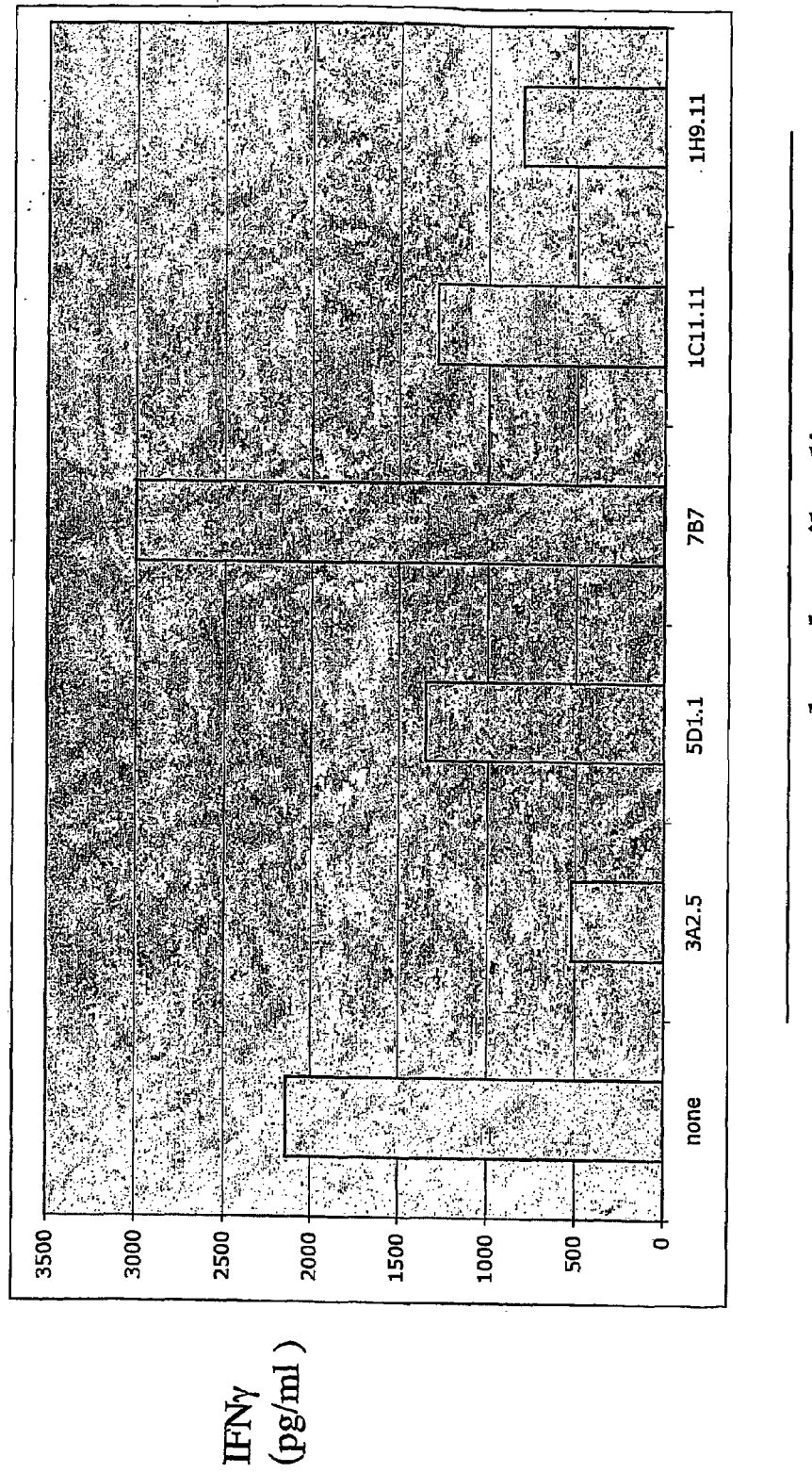
FIG. 8 is a histogram summarizing data on IFNγ production in mouse MLR cultures. Irradiated Balb/c splenocytes were used to stimulate splenocytes derived from C57B16 mice. After 48 h in culture the supernatants were harvested and used to measure IFNγ levels. Treatment of the cultures with mAbs 3A2 and 1H9 during incubation significantly reduced the level of IFNγ secreted into the supernatant.
Figure 9:
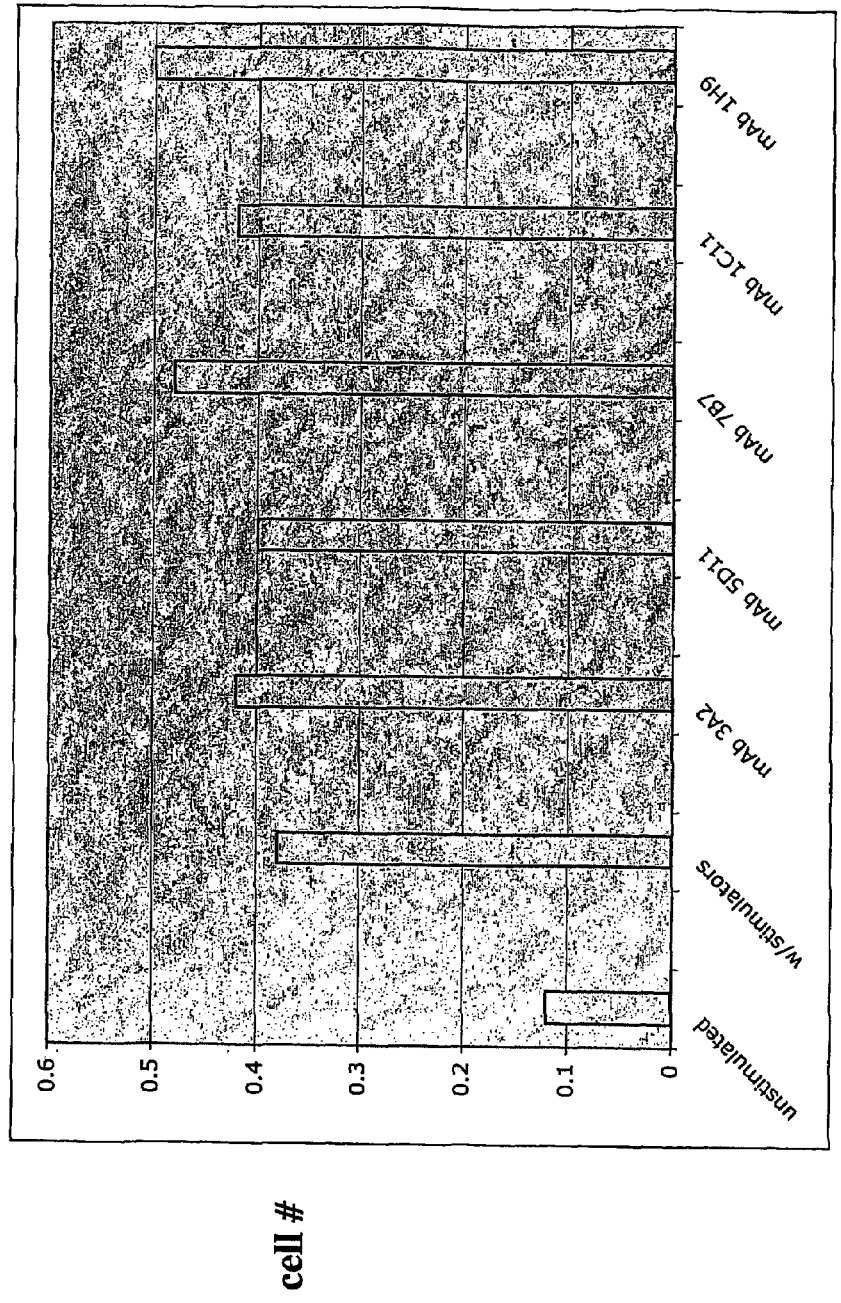
FIG. 9 is a histogram summarizing data on cell proliferation in mouse MLR cultures. Irradiated Balb/c splenocytes were used to stimulate splenocytes derived from C57B16 mice. After 72 h in culture a vital dye was added to the cultures, and allowed to develop for 1-4 hours. Treatment of the cultures with anti-KIM-1 antibodies during the 3 day culturing period did not affect cell proliferation.

Treatment of the MLR culture with the rat anti-mouse KIM-1 mAbs 3A2.5 and 1H19.11 significantly reduced the level of IFNγ secreted into the supernatant (FIG. 8). This effect was specific for IFNγ, since no decrease in the level of Il-2 or TNF secreted into the supernatant was observed. The effect was not due to decreased cell number in these cultures, since the cell proliferation assay showed that the number of live cells in the cultures was similar (FIG. 9).

Figure 10:
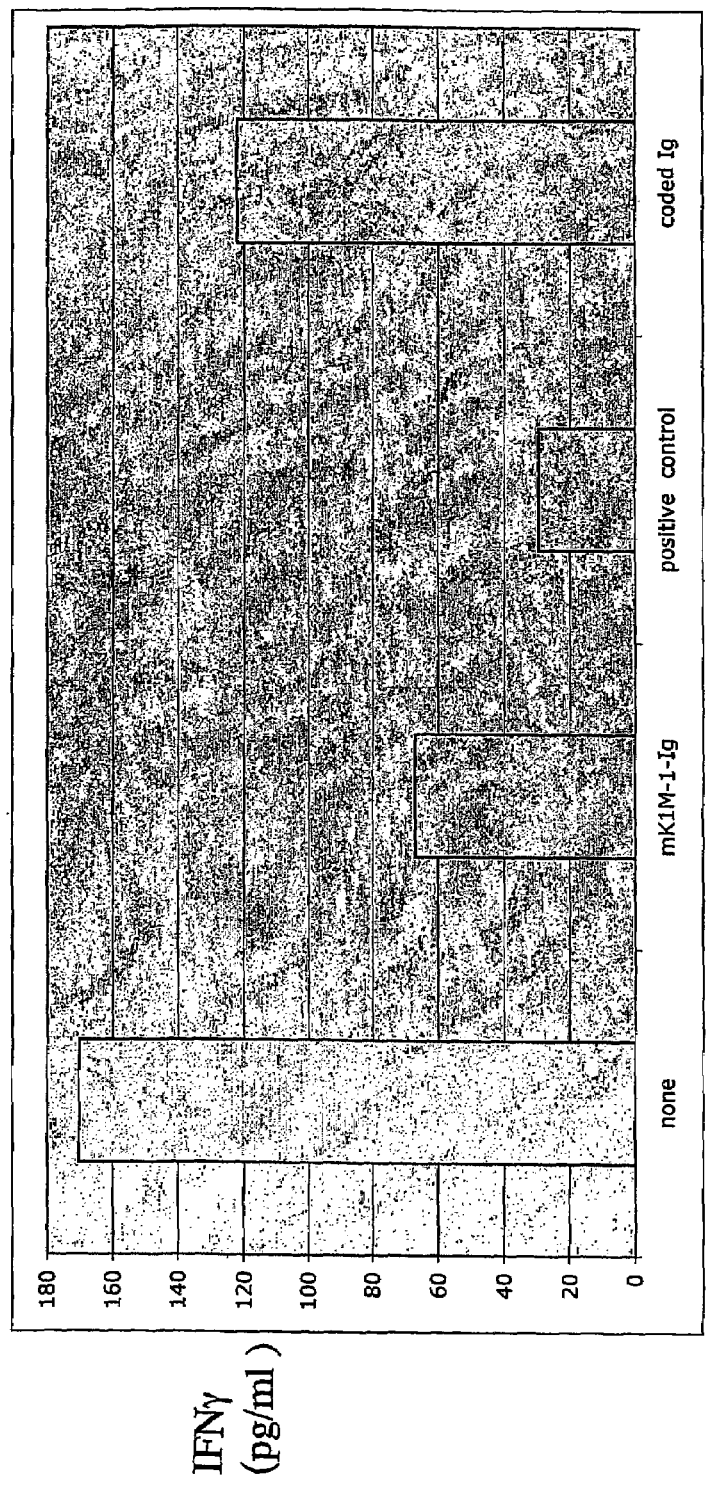
FIG. 10 is a histogram summarizing data on IFNγ production in mouse MLR cultures. Irradiated Balb/c splenocytes were used to stimulate splenocytes derived from C57B16 mice. After 48 h in culture the supernatants were harvested and used to measure IFNγ levels. Treatment of the cultures with KIM-1-Ig fusion protein during incubation significantly reduced the level of IFNγ secreted into the supernatant.
Figure 11:
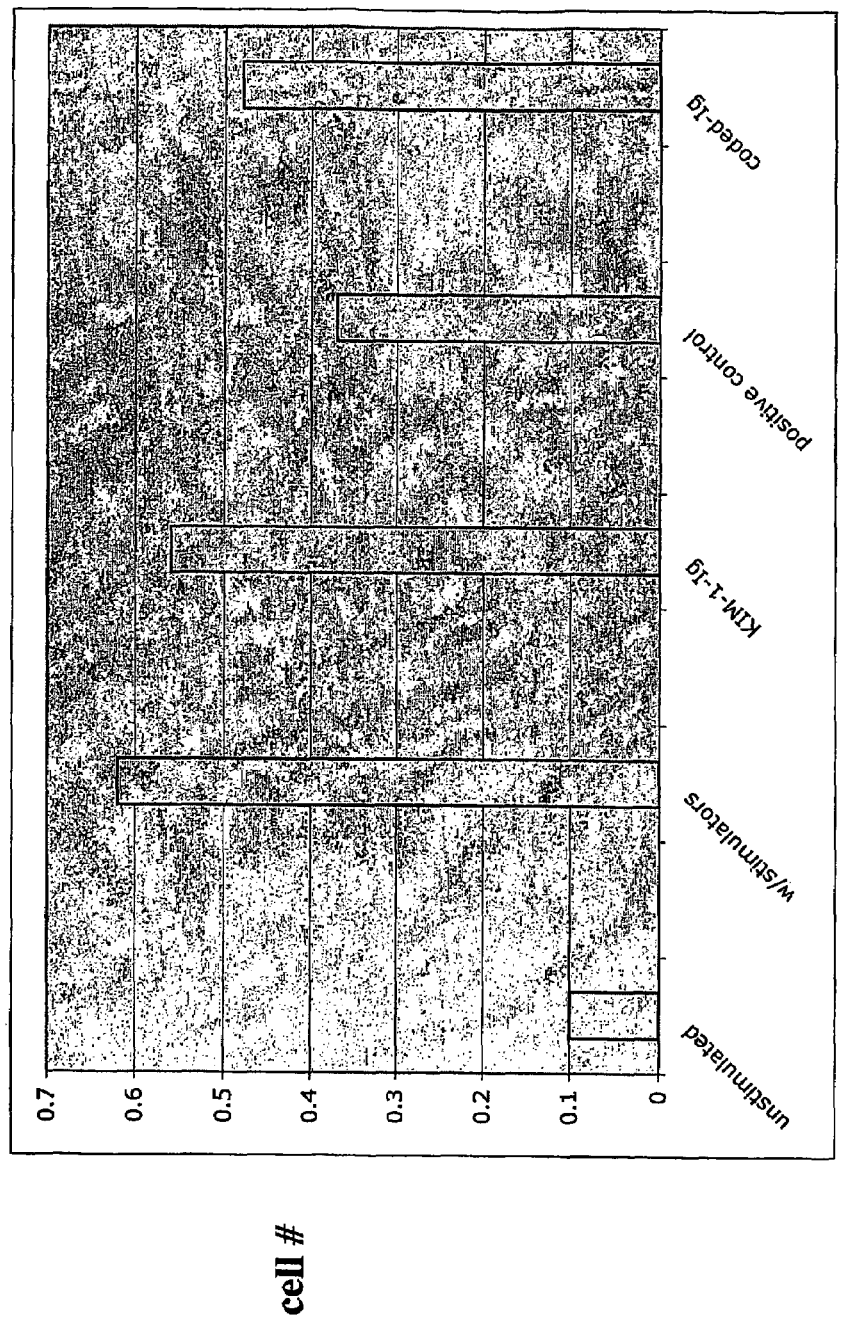
FIG. 11 is a histogram summarizing data on cell proliferation in mouse MLR cultures. Irradiated Balb/c splenocytes were used to stimulate splenocytes derived from C57B1/6 mice. After 72 h in culture a vital dye was added to the cultures, and allowed to develop for 1-4 hours. Treatment of the cultures with KIM-1-Ig fusion protein during the 3 day culturing period did not affect cell proliferation.

Treatment of the MLR culture with KIM-1-Ig fusion protein significantly reduced the level of IFNγ secreted into the supernatant (FIG. 10). This effect was specific for IFNγ, since no decrease in the level of Il-2 or TNF secreted into the supernatant was noted (data not shown). The effect was not due to decreased cell number in these cultures, since the cell proliferation assay showed that the number of live cells in the culture treated with KIM-1-Ig fusion protein was very similar to the untreated control (FIG. 11).

Human MLR assays and antagonism of KIM-1. Mixed lymphocyte reactions (MLR) were run as follows: Peripheral blood mononuclear cells were isolated from whole blood taken from normal human donors using Ficoll gradient centrifugation. The cells were then washed with sterile, pyrogen-free PBS, and centrifuged to pellet the cells. The cells were resuspended in the PBS solution a second time, pelleted again, then resuspended in complete RPMI media. The cells were counted and diluted as necessary. JY cells (ATCC, Bethesda, Md. USA) were used as the stimulator cells, therefore, these were irradiated at 10000 RAD prior to use.

To set up the assays, stimulator were added to the well as varying ratios relative to the number of responder cells ($2 \times 10^5$/well). Media was supplemented with mouse anti-KIM-1 antibodies, at 20 µg/ml, as indicated. Cultures were set up in three identical plates, and each experimental condition was represented by 3 wells per plate. One plate was used to generate cell proliferation data using an MTS assay (CellTiter 96, Promega, Madison, Wis. USA). The other plates were used to collect supernatant samples for cytokine analyses. ELISAs (Pierce Endogen, Rockford, Ill. USA or R+D Systems, Minneapolis, Minn. USA) were used to measure the levels of hIFNγ, hTNF, and hIl-2 in culture supernatants.

Standard errors for values derived from the proliferation assays and ELISAs were less than 10%, and have been omitted from the figures. Large deviations from the positive control values for IFNγ were observed, while the levels of Il-2 and TNF in the cultures were not significantly different between the positive control and treatment groups. The TNF data have been omitted. Data for Il-2, IFNγ and cell proliferation are shown for this representative experiment.

Figure 12A:
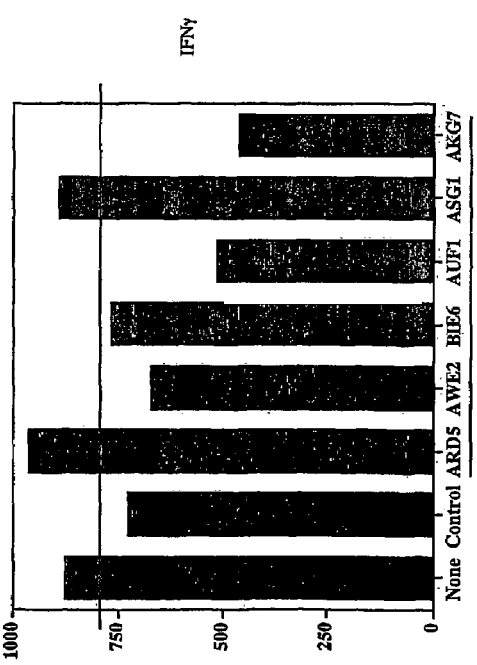
FIGS. 12A and 12B are histograms summarizing data on IFNγ production in human MLR cultures. Irradiated JY cells were used to stimulate peripheral blood mononuclear cells from a normal human donor. After 5 days in culture the supernatants were harvested and used to measure IFNγ and Il-2 levels. Treatment of the cultures with mAbs AUF1 and AKG7 during incubation significantly reduced the level of IFNγ secreted into the supernatant (FIG. 12A), while the level of Il-2 produced remained unchanged (FIG. 12B).
Figure 12B:
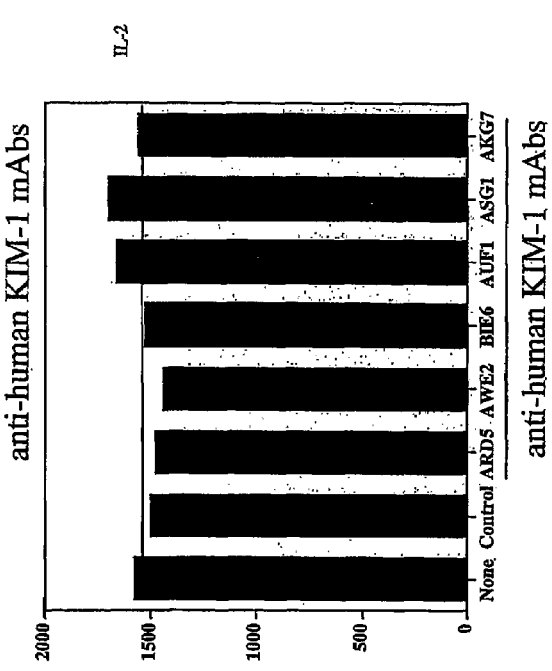
Figure 13:
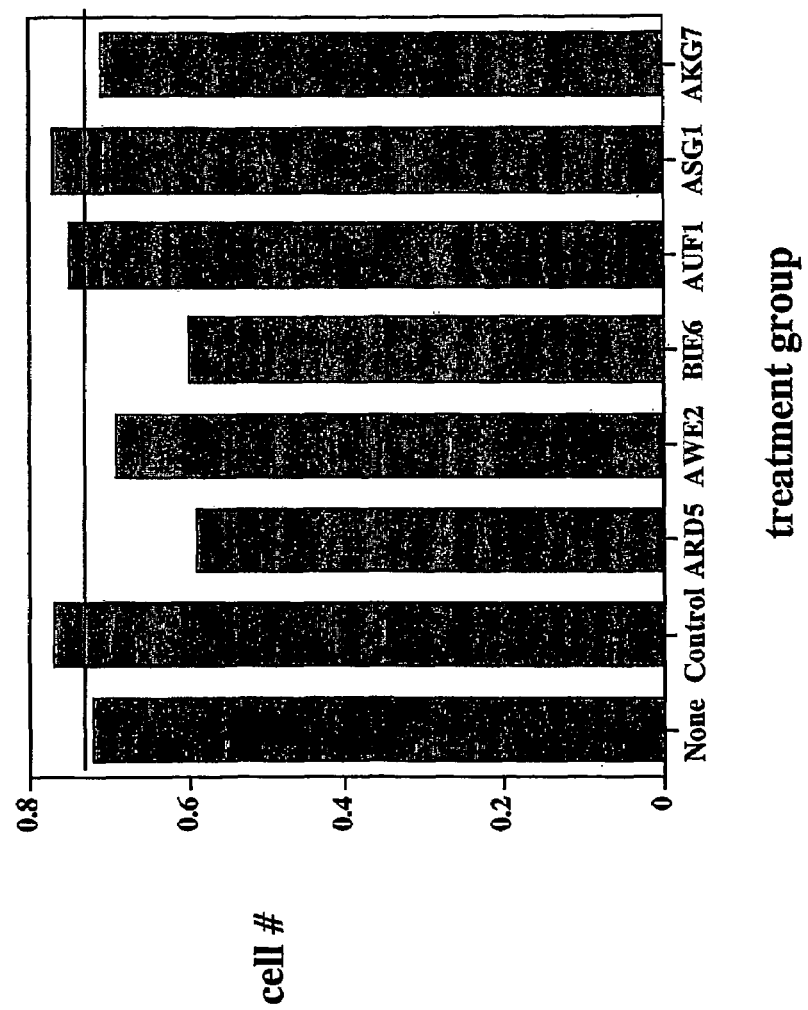
FIG. 13 is a histogram summarizing data on cell proliferation in human MLR cultures. Irradiated JY cells were used to stimulate peripheral blood mononuclear cells from a normal human donor. After 6 days in culture a vital dye was added to the cultures, and allowed to develop for 1-4 hours. Treatment of the cultures with anti-human KIM-1 mAbs during the 6 day culturing period did not significantly effect cell proliferation.

Treatment of the MLR culture with the mouse anti-human KIM-1 mAbs AUF1 and AKG7 significantly reduced the level of IFNγ secreted into the supernatant (FIG. 12A). This effect was specific for IFNγ, since no decrease in the level of Il-2 or TNF secreted into the supernatant was noted (FIG. 12B). The effect was not due to decreased cell number in these cultures, since the cell proliferation assay showed the number of live cells in the cultures to be similar (FIG. 13).

Example 12

Mouse Inflammatory Bowel Disease (IBD) Model

The ability of a soluble form of KIM-1-Ig fusion protein to influence the course or severity of symptoms in a model of IBD in experimental mice. In this model, DSS was used to chronically irritate the large bowel (colon), causing inflammation to develop. It was known that pro-inflammatory mediators such as IFNγ, TNF, and Il-12 are important to the development and severity of IBD, both in mouse models and in human patients (Egger et al., 2000, *Digestion* 62:240-248; Monteleone et al., 2000, *Ann. Med.* 32:552-560; Bouma et al., 2003, *Nat. Rev. Immunol.* 3:521-533). As described above, MLR data had suggested that KIM-1 modulation could influence the production of proinflammatory mediators such as IFNγ. Therefore, a KIM-1-modifying reagent was tested in vivo. It was hypothesized that the KIM-1-Ig fusion protein was acting by interrupting the interaction of one or more ligands with KIM-1 expressed on cells such as activated lymphocytes or other immune cells.

IBD was induced in mice using the dextran sulfate sodium (DSS) model (Copper et al., 1993, *Lab. Invest.* 69:238-249). A solution of 4.5% DSS (ICN Biomedicals, Aurora Ohio USA) in sterile distilled water was provided as the drinking source. Mice were wighed just prior to introduction to DSS, and weighed daily thereafter. Mice were also scored for extent of diarrhea (1: soft pellet, 2: loose pellet, 3: overtly fluid feces, 4: gross incontinence) and for the presence of blood in the feces (0: none, 1: blood) using the ColoScreen slides (Helena Labs, Beaumont Tex. USA). Small, but detectable, amounts of blood were given an intermediate score of 0.5. Mice were dosed ip with 200 μs of KIM-1-Ig fusion protein or polyclonal hIgG control (SandImmune, Sandoz, Geneva Switzerland) on day 0, day 2, and day 5. On day 8, mice were taken off of DSS-water, and given normal drinking water. Monitoring for weight and clinical scores continued until day 12, at which time the experiment ended.

Figure 14:
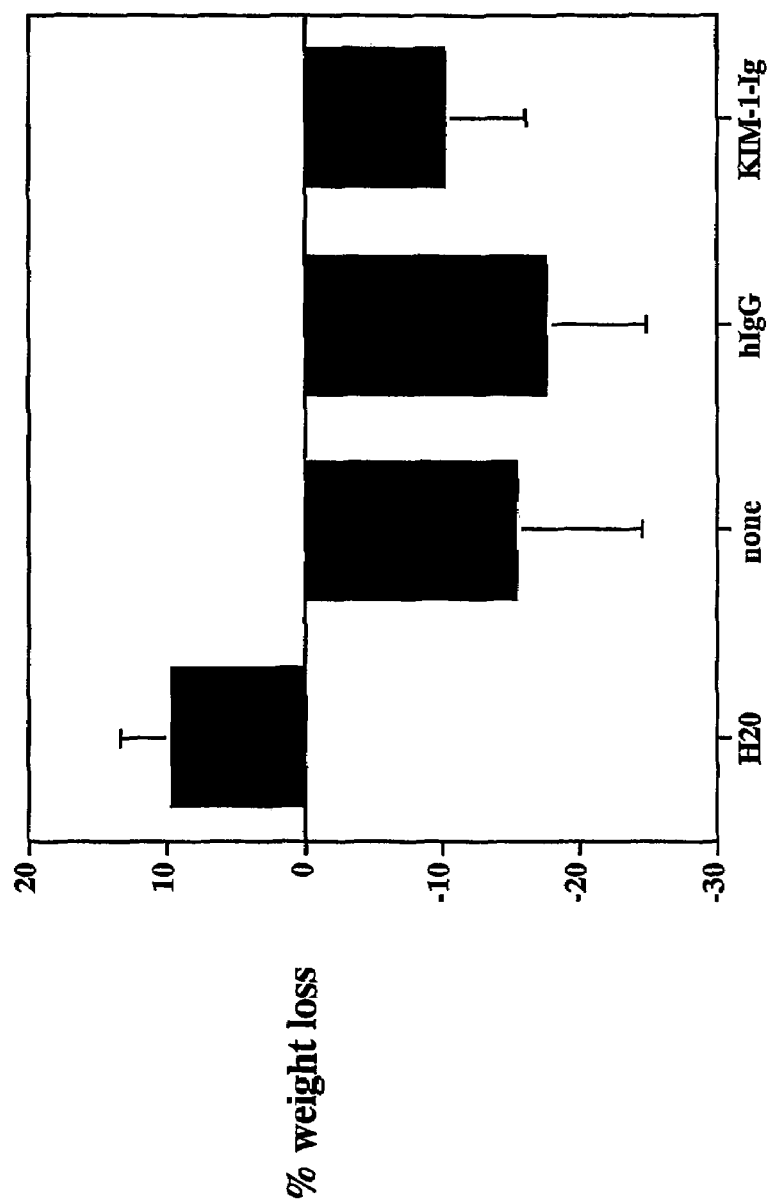
FIG. 14 is a histogram summarizing data on weight loss following induction of inflammatory bowel disease in mice. Female Balb/c mice were exposed to dextran sulfate sodium (DSS). After 8 days, mice were switched back onto plain water and allowed to recover from DSS exposure. Three days later, the mice were weighed. The weight was calculated as percent of weight at the start of the experiment. Treatment with the KIM-1-Ig fusion protein conferred significant protection to mice, as indicated by the improvement in the weight score. There were 10 mice/group. A test of the equivilence of the means gave a significance of >p=0.0001.
Figure 15B:
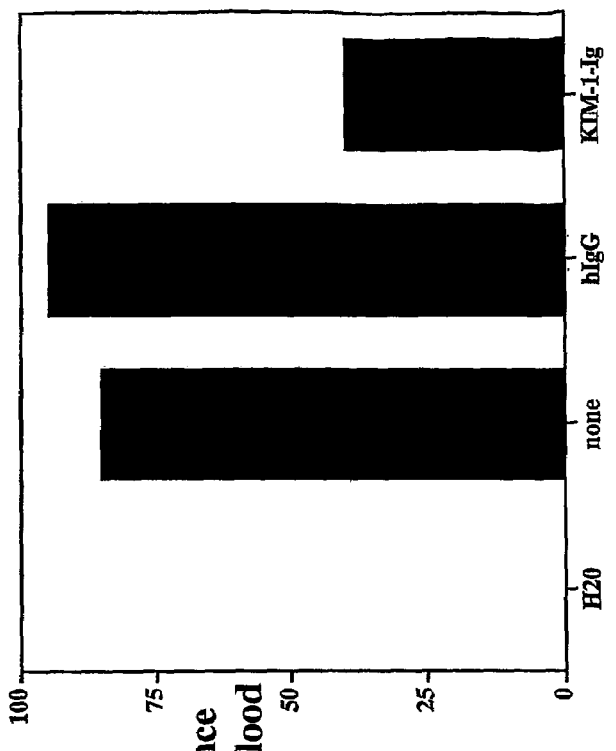
FIGS. 15A and 15B are histograms summarizing clinical score data following induction of inflammatory bowel disease in mice. After a 3-day recovery period, mice were assessed for diarrhea and the presence of blood in the feces. Mice treated with KIM-1-Ig fusion protein had a significantly better score than untreated or control-Ig treated groups (FIG. 15A). This was due in part to significantly fewer mice having blood present in the fecal pellets (FIG. 15B). The means equivilence tests gave a significant value for the differences in the clinical score (p=0.05) of unteated controls as compared to KIM-1-Ig treated cohorts.
Figure 15A:
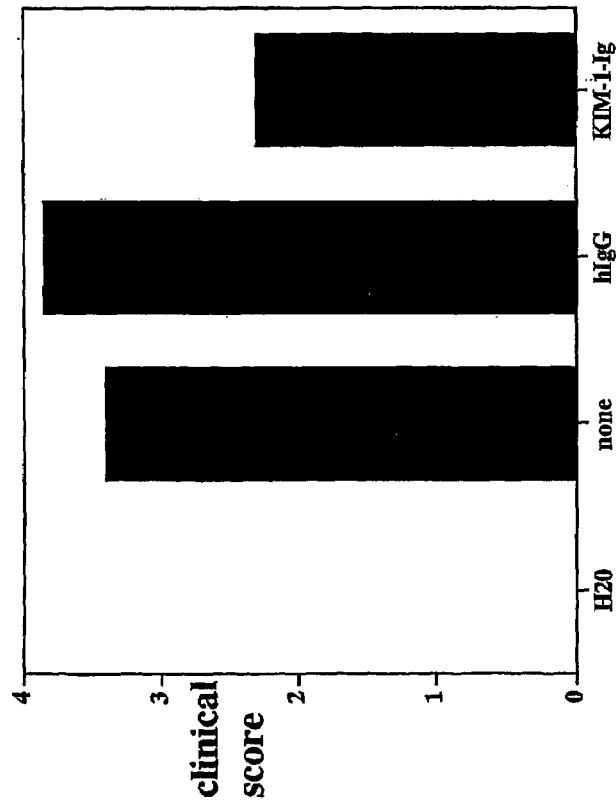

Treatment of mice during the induction phase of IBD (days 0, 2 and 5) had a significant impact on cumulative weight loss and disease score, up to and including day 8. Therefore, mice were taken off of DSS and returned to normal drinking water, and their recovery was monitored. Mice that had received KIM-1-Ig fusion protein on days 0, 2 and 5 were consistently healthier on day 11 (3 days into recovery) as indicated by the extent of weight loss (FIG. 14) and by their clinical score (diarrhea and bleeding; FIG. 15A). Many fewer mice in the KLM-1-Ig-treated cohort had blood present in the stool (FIG. 15B).

These data suggested that KIM-1 modulation in vivo has protective effects in an acute inflammatory context, such as is present after DSS insult to the gut mucosa. These results suggested that KIM-1 antagonists will be efficacious in other acute or chronic inflammatory settings, e.g., in rheumatoid arthritis, multiple sclerosis, psoriasis and pancreatitis.

Other embodiments are within the following claims.

The invention claimed is:

1. A method of treating an immunological disorder in a subject, the method comprising administering to the subject an effective amount of a composition comprising an antagonist antibody or antigen-binding fragment thereof that binds to KIM-1, wherein the immunological disorder is an inflammatory bowel disease.

2. The method of claim 1, wherein the antibody or antigen-binding fragment thereof is a polyclonal antibody, monoclonal antibody, humanized antibody, fully human antibody, chimeric antibody, single-chain antibody, diabody, Fab fragment, Fab' fragment, F(ab')₂ fragment, Fv fragment, Fd fragment, dAb fragment, or complementarity determining region-containing fragment.

3. The method of claim 1, wherein the inflammatory bowel disease is Crohn's disease, ulcerative colitis, or ileitis.

4. The method of claim 3, wherein the antibody or antigen-binding fragment thereof is a polyclonal antibody, monoclonal antibody, humanized antibody, fully human antibody, chimeric antibody, single-chain antibody, diabody, Fab fragment, Fab' fragment, F(ab')₂ fragment, Fv fragment, Fd fragment, dAb fragment, or complementarity determining region-containing fragment.

* * * * *

UNITED STATES PATENT AND TRADEMARK OFFICE
CERTIFICATE OF CORRECTION

| | | |
|---|---|---|
| PATENT NO. | : 7,597,887 B2 | Page 1 of 1 |
| APPLICATION NO. | : 10/540959 | |
| DATED | : October 6, 2009 | |
| INVENTOR(S) | : Paul D. Rennert | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 542 days.

Signed and Sealed this
Eighth Day of March, 2011

David J. Kappos
*Director of the United States Patent and Trademark Office*